(12) United States Patent
Scales

(10) Patent No.: US 8,338,112 B1
(45) Date of Patent: Dec. 25, 2012

(54) ANTI-HEDGEHOG ANTIBODIES

(75) Inventor: Suzanna J. Scales, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/584,711

(22) Filed: Aug. 13, 2012

Related U.S. Application Data

(60) Continuation of application No. 13/217,191, filed on Aug. 24, 2011, now abandoned, which is a division of application No. 12/341,910, filed on Dec. 22, 2008, now Pat. No. 8,030,454.

(60) Provisional application No. 61/017,232, filed on Dec. 28, 2007, provisional application No. 61/099,864, filed on Sep. 24, 2008.

(51) Int. Cl.
*G01N 33/53* (2006.01)

(52) U.S. Cl. ... 435/7.1; 530/350; 530/387.1; 530/387.3; 530/387.7; 530/387.9; 435/7.21; 435/7.23; 435/40.52

(58) Field of Classification Search ............ 435/7.1, 435/7.21, 7.23, 40.52; 530/350, 387.1, 387.3, 530/387.7, 387.9
See application file for complete search history.

(56) References Cited

OTHER PUBLICATIONS

Cengel (Cancer Biol Ther. Feb. 2004; 3 (2): 165-6).*
Feng et al. (Clin. Cancer Res. Mar. 1, 2007; 13 (5): 1389-98).*

* cited by examiner

*Primary Examiner* — Stephen Rawlings
(74) *Attorney, Agent, or Firm* — Brian L. Buckwalter

(57) ABSTRACT

The invention relates to anti-hedgehog antibodies, their use in the detection of hedgehog expression in tissue, and to the use of such detection in the treatment of cancer.

3 Claims, 14 Drawing Sheets

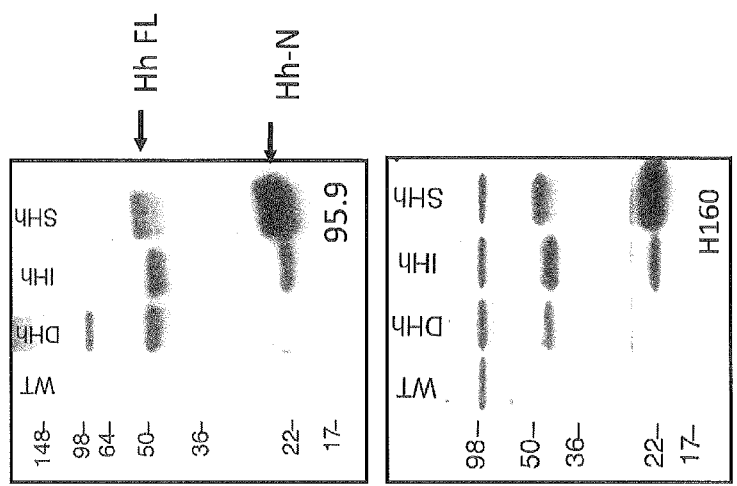
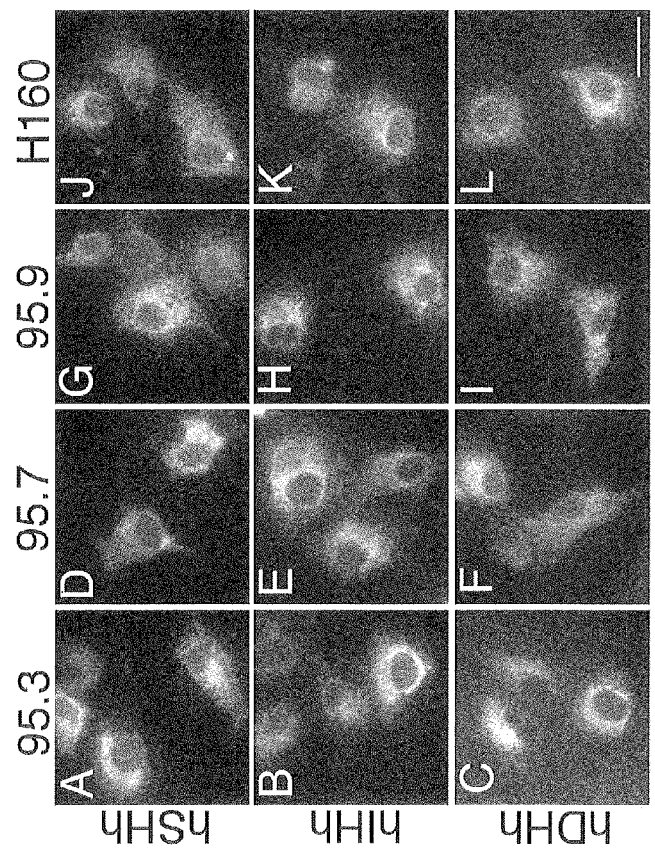

Figure 4A

Light chains (Excluding 23aa signal sequence):

| Aa# (after ss) | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 |
|---|---|---|---|---|---|---|---|---|---|---|---|---|---|---|---|---|---|---|---|---|---|---|---|---|---|
| 95.9 LC cloned | A | V | L | T | Q | T | P | S | P | V | S | A | A | V | G | G | T | V | T | I | N | C | Q | S | S |
| 95.9 LC rMab | A | V | L | T | Q | T | P | S | P | V | S | A | A | V | G | G | T | V | T | I | N | C | Q | S | (S) |
| 95.3 LC rMab | A | V | L | T | Q | T | P | S | - | V | - | A | A | V | G | - | - | - | (I) | I | - | - | - | - | - |
| 95.7 LC rMab | A | V | L | T | Q | T | P | S | P | V | S | A | A | V | G | G | T | V | T | I | N | C | Q | S | (S) |

Figure 4B

Heavy chains (excluding 19aa signal sequence)

| Aa# (after ss) | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|
| 95.9 HC cloned | Q | S | V | K | E | S | G | G | G | L | V | Q | P | E | G | S | L | T | L | T | C | T | V | S | G |
| 95.9 HC rMab | (Q) | L | V | K | E | G | G | G | A | L | V | Q | L | V | K | S | L | T | L | T | E | L | V | S | G |
| " seq 2 | | | E | Q | S | S | - | - | - | E | V | (G) | P | E | G | P | G | (G) | - | T | C | - | - | - | - |
| 95.3 HC rMab | (Q) | L | V | K | E | G | G | - | A | L | (V) | Q | L | V | K | S | L | T | (S) | - | E | L | - | - | (S) |
| " seq 2 | | | E | S | S | - | G | - | - | E | V | G | - | (E) | (G) | P | G | - | - | - | E | - | - | - | - |
| 95.7 HC rMab | (Q) | L | V | K | E | S | G | - | A | L | V | Q | P | V | K | P | G | T | - | T | C | - | - | - | - |
| " seq 2 | | | E | Q | S | - | G | - | - | E | G | - | P | E | G | - | G | - | - | - | - | - | - | - | - |

Figure 5

|  | | | |
|---|---|---|---|
| Shh_human | 24 | CGPGRG-FG-KRRHPKKLTPLAY | 44 |
| Ihh_human |  | CGPGRV-VGSRRRPPRKLVPLAY | 49 |
| Dhh_human |  | CGPGRGPVGRRRYARKQLVPLLY | 45 |

|  | | | |
|---|---|---|---|
| Shh_human | 45 | KQFIPNVAKTLGASGRYGKISRNS RFK LTPNYNP IIFK NTGA | 94 |
| Ihh_human | 50 | KQFSPNVPKTLGASGRYGKIARSS RFK LTPNYNP IIFK NTGA | 99 |
| Dhh_human | 46 | KQFVPGVPRLGASGPAGRVARGS RFRD LVPNYNP IIFK NSGA | 95 |

|  | | | |
|---|---|---|---|
| Shh_human | 95 | RLMTQRCK KLNALAISV NQWPGVKLRVT GW GHHS SLHY GR | 144 |
| Ihh_human | 100 | RLMTQRCK RLNSLAISV NQWPGVKLRVT GW GHHS SLHY GR | 149 |
| Dhh_human | 96 | RLMTERCK ERVNALAIAV NMMPGVRLRVT GW GHHAQDS LHY GR | 145 |

|  | | | |
|---|---|---|---|
| Shh_human | 145 | ITTS RSKYGMLARLAV AGF WVYY SKAHIHCSVKA NSVAAK | 194 |
| Ihh_human | 150 | AV ITTS RNKYGLLARLAV AGF WVYY SKAHVHCSVKS HSAAK | 199 |
| Dhh_human | 146 | AL ITTS RNKYGLLARLAV AGF WVYY SRNHVHVSVKADNS LAVR | 195 |

|  | | | |
|---|---|---|---|
| Shh_human | 195 | SGG | 197 |
| Ihh_human | 200 | TGG |  |
| Dhh_human | 196 | AGG |  |

Fig 7
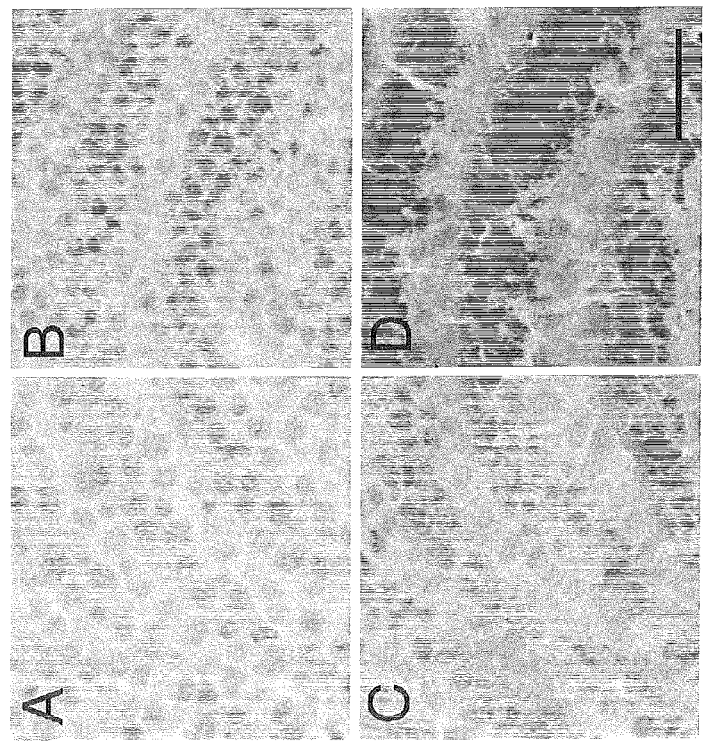
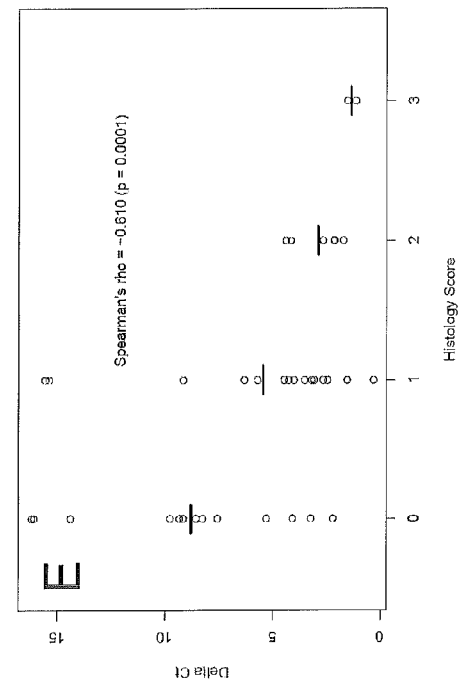
A) 0+ staining (negative)
B) 1+ staining (weak)
C) 2+ staining (moderate)
D) 3+ staining (strong)

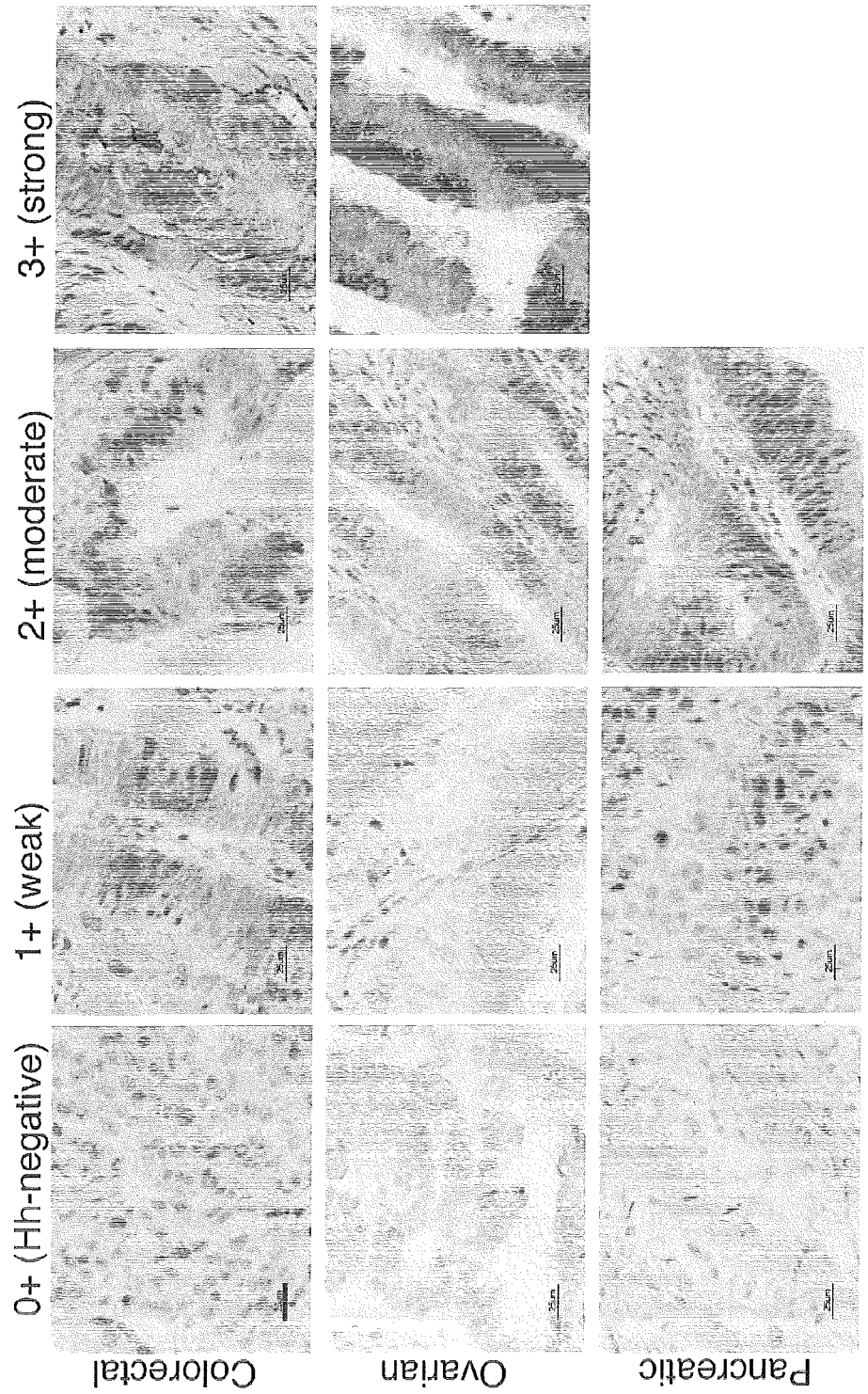

Fig 9B

| | \multicolumn{7}{c|}{IHC Score} | |
| | 0 | | 1 | | 2 | | 3 | | Total |
| | n | freq | n | freq | n | freq | n | freq | n |
| Colon Adenocarcinoma | 18 | 18% | 68 | 69% | 10 | 10% | 3 | 3% | 99 |
| Metastatic CRC | 10 | 20% | 38 | 76% | 2 | 4% | 0 | 0% | 50 |
| Ovarian Adenocarcinoma | 5 | 7% | 41 | 57% | 22 | 31% | 4 | 6% | 72 |
| Pancreatic Tumors | 24 | 23% | 74 | 70% | 7 | 7% | 0 | 0% | 105 |

Fig 11A

Signal sequence (GNE's)

MGWSCIILFLVATATGAYAQSVKESGGGLVQPEGSLTLTCTVS
GFSLSSYDMSWVRQAPGSGLEWIGGILSGGSAYYASWAKSR
STITKNLNTVTLKMTSLTAADTATYFCARGIYPVGTNYNWG
PGTLVTVSSG**QPKAPSVFPLAPCCGDTPSSTVTLGCLVKGY
LPEPVTVTWNSGTLTNGVRTFPSVRQSSGLYSLSSVVSVTSS
SQPVTCNVAHPATNTKVDKTVAPSTCSK*PTCPPPPELLGGPS
VFIFPPKPKDTLMISRTPEVTCVVVDVSQDDPEVQFTWYINNE
QVRTARPPLREQQFNSTIRVVSTLPIAHQDWLRGKEFKCKVH
NKALPAPIEKTISKARGQPLEPKVYTMGPPREELSSRSVSLTC
MINGFYPSDISVEWEKNGKAEDNYKTTPAVLDSDGSYFLYSK
LSVPTSEWQRGDVFTCSVMHEALHNHYTQKSISRSPGK

- CDR1
- CDR2
- CDR3

** Start of rabbit antibody constant region backbone
* Start of Fc region

Fig 11B

Signal sequence (GNE's)

MGWSCIILFLVATATGVHSDIAVLTQTPSPVSAAVG
GTVTINCQSSPSVYSNYLAWYQQKPGQPPKLLI
YYASTLASGVPSRFKGSGSGTEFTLTISDLECADAA
TYYCAGGYIDTSDTAFGGGTEVVKGDPVAPTVLIF
PPAADQVATGTVTIVCVANKYFPDVTVTWEVDGTT
QTTGIENSKTPQNSADCTYNLSSTLTSTQYNSHK
EYTCKVTQGTTSVVQSFNRGDC

- CDR1
- CDR2
- CDR3

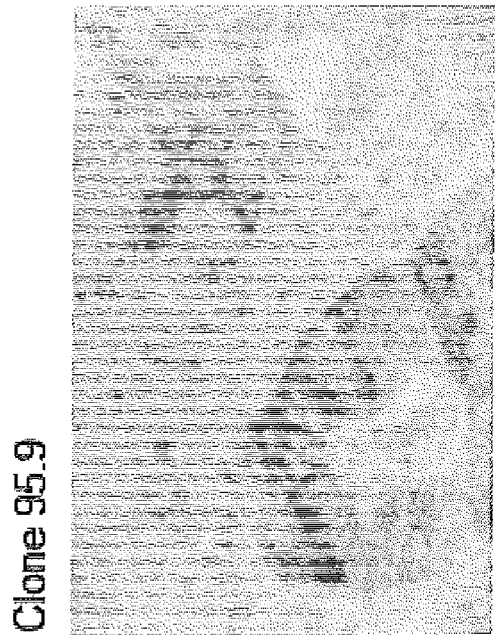
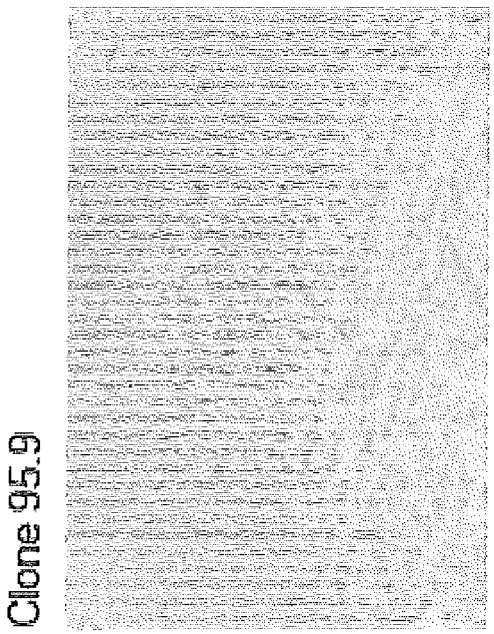
Fig 12

SEQUENCE LISTING

```
<160> NUMBER OF SEQ ID NOS: 18

<210> SEQ ID NO 1
<211> LENGTH: 24
<212> TYPE: PRT
<213> ORGANISM: Mus musculus

<400> SEQUENCE: 1

Gln Ser Val Lys Glu Ser Gly Gly Gly Leu Val Gln Pro Glu Gly
 1               5                  10                  15

Ser Leu Thr Leu Thr Cys Thr Val Ser
                20

<210> SEQ ID NO 2
<211> LENGTH: 10
<212> TYPE: PRT
<213> ORGANISM: Mus musculus

<400> SEQUENCE: 2

Gly Phe Ser Leu Ser Ser Tyr Asp Met Ser
                 5                  10

<210> SEQ ID NO 3
<211> LENGTH: 13
<212> TYPE: PRT
<213> ORGANISM: Mus musculus

<400> SEQUENCE: 3

Trp Val Arg Gln Ala Pro Gly Ser Gly Leu Glu Trp Ile
                 5                  10

<210> SEQ ID NO 4
<211> LENGTH: 17
<212> TYPE: PRT
```

<213> ORGANISM: Mus musculus

<400> SEQUENCE: 4

Gly Gly Ile Leu Ser Gly Gly Ser Ala Tyr Tyr Ala Ser Trp Ala
 1               5                  10                  15

Lys Ser

<210> SEQ ID NO 5
<211> LENGTH: 30
<212> TYPE: PRT
<213> ORGANISM: Mus musculus

<400> SEQUENCE: 5

Arg Ser Thr Ile Thr Lys Asn Thr Asn Leu Asn Thr Val Thr Leu
 1               5                  10                  15

Lys Met Thr Ser Leu Thr Ala Ala Asp Thr Ala Thr Tyr Phe Cys
                20                  25                  30

<210> SEQ ID NO 6
<211> LENGTH: 13
<212> TYPE: PRT
<213> ORGANISM: Mus musculus

<400> SEQUENCE: 6

Ala Arg Gly Ile Tyr Pro Val Gly Thr Asn Tyr Asn Ile
 1               5                  10

<210> SEQ ID NO 7
<211> LENGTH: 12
<212> TYPE: PRT
<213> ORGANISM: Mus musculus

<400> SEQUENCE: 7

Trp Gly Pro Gly Thr Leu Val Thr Val Ser Ser Gly
 1               5                  10

<210> SEQ ID NO 8
<211> LENGTH: 322
<212> TYPE: PRT
<213> ORGANISM: Mus musculus

<400> SEQUENCE: 8

Gln Pro Lys Ala Pro Ser Val Phe Pro Leu Ala Pro Cys Cys Gly
 1               5                  10                  15

Asp Thr Pro Ser Ser Thr Val Thr Leu Gly Cys Leu Val Lys Gly
                20                  25                  30

Tyr Leu Pro Glu Pro Val Thr Val Thr Trp Asn Ser Gly Thr Leu
                35                  40                  45

Thr Asn Gly Val Arg Thr Phe Pro Ser Val Arg Gln Ser Ser Gly
                50                  55                  60

Leu Tyr Ser Leu Ser Ser Val Val Ser Val Thr Ser Ser Ser Gln
                65                  70                  75

Pro Val Thr Cys Asn Val Ala His Pro Ala Thr Asn Thr Lys Val
                80                  85                  90

Asp Lys Thr Val Ala Pro Ser Thr Cys Ser Lys Pro Thr Cys Pro
                95                 100                 105

Pro Pro Glu Leu Leu Gly Gly Pro Ser Val Phe Ile Phe Pro Pro
               110                 115                 120

Lys Pro Lys Asp Thr Leu Met Ile Ser Arg Thr Pro Glu Val Thr
               125                 130                 135

-continued

```
Cys Val Val Val Asp Val Ser Gln Asp Asp Pro Glu Val Gln Phe
            140                 145                 150

Thr Trp Tyr Ile Asn Asn Glu Gln Val Arg Thr Ala Arg Pro Pro
            155                 160                 165

Leu Arg Glu Gln Gln Phe Asn Ser Thr Ile Arg Val Val Ser Thr
            170                 175                 180

Leu Pro Ile Ala His Gln Asp Trp Leu Arg Gly Lys Glu Phe Lys
            185                 190                 195

Cys Lys Val His Asn Lys Ala Leu Pro Ala Pro Ile Glu Lys Thr
            200                 205                 210

Ile Ser Lys Ala Arg Gly Gln Pro Leu Glu Pro Lys Val Tyr Thr
            215                 220                 225

Met Gly Pro Pro Arg Glu Glu Leu Ser Ser Arg Ser Val Ser Leu
            230                 235                 240

Thr Cys Met Ile Asn Gly Phe Tyr Pro Ser Asp Ile Ser Val Glu
            245                 250                 255

Trp Glu Lys Asn Gly Lys Ala Glu Asp Asn Tyr Lys Thr Thr Pro
            260                 265                 270

Ala Val Leu Asp Ser Asp Gly Ser Tyr Phe Leu Tyr Ser Lys Leu
            275                 280                 285

Ser Val Pro Thr Ser Glu Trp Gln Arg Gly Asp Val Phe Thr Cys
            290                 295                 300

Ser Val Met His Glu Ala Leu His Asn His Tyr Thr Gln Lys Ser
            305                 310                 315

Ile Ser Arg Ser Pro Gly Lys
            320

<210> SEQ ID NO 9
<211> LENGTH: 24
<212> TYPE: PRT
<213> ORGANISM: Mus musculus

<400> SEQUENCE: 9

Asp Ile Ala Val Leu Thr Gln Thr Pro Ser Pro Val Ser Ala Ala
 1               5                  10                  15

Val Gly Gly Thr Val Thr Ile Asn Cys
                20

<210> SEQ ID NO 10
<211> LENGTH: 12
<212> TYPE: PRT
<213> ORGANISM: Mus musculus

<400> SEQUENCE: 10

Gln Ser Ser Pro Ser Val Tyr Ser Asn Tyr Leu Ala
                5                   10

<210> SEQ ID NO 11
<211> LENGTH: 14
<212> TYPE: PRT
<213> ORGANISM: Mus musculus

<400> SEQUENCE: 11

Trp Tyr Gln Gln Lys Pro Gly Gln Pro Pro Lys Leu Leu Ile
                5                   10

<210> SEQ ID NO 12
<211> LENGTH: 8
<212> TYPE: PRT
<213> ORGANISM: Mus musculus
```

<400> SEQUENCE: 12

Tyr Tyr Ala Ser Thr Leu Ala Ser
                5

<210> SEQ ID NO 13
<211> LENGTH: 32
<212> TYPE: PRT
<213> ORGANISM: Mus musculus

<400> SEQUENCE: 13

Gly Val Pro Ser Arg Phe Lys Gly Ser Gly Ser Gly Thr Glu Phe
 1               5                  10                  15

Thr Leu Thr Ile Ser Asp Leu Glu Cys Ala Asp Ala Ala Thr Tyr
                20                  25                  30

Tyr Cys

<210> SEQ ID NO 14
<211> LENGTH: 11
<212> TYPE: PRT
<213> ORGANISM: Mus musculus

<400> SEQUENCE: 14

Ala Gly Gly Tyr Ile Asp Thr Ser Asp Thr Ala
                5                  10

<210> SEQ ID NO 15
<211> LENGTH: 114
<212> TYPE: PRT
<213> ORGANISM: Mus musculus

<400> SEQUENCE: 15

Phe Gly Gly Gly Thr Glu Val Val Lys Gly Asp Pro Val Ala
 1               5                  10                  15

Pro Thr Val Leu Ile Phe Pro Pro Ala Ala Asp Gln Val Ala Thr
                20                  25                  30

Gly Thr Val Thr Ile Val Cys Val Ala Asn Lys Tyr Phe Pro Asp
                35                  40                  45

Val Thr Val Thr Trp Glu Val Asp Gly Thr Thr Gln Thr Thr Gly
                50                  55                  60

Ile Glu Asn Ser Lys Thr Pro Gln Asn Ser Ala Asp Cys Thr Tyr
                65                  70                  75

Asn Leu Ser Ser Thr Leu Thr Leu Thr Ser Thr Gln Tyr Asn Ser
                80                  85                  90

His Lys Glu Tyr Thr Cys Lys Val Thr Gln Gly Thr Thr Ser Val
                95                 100                 105

Val Gln Ser Phe Asn Arg Gly Asp Cys
                110

<210> SEQ ID NO 16
<211> LENGTH: 174
<212> TYPE: PRT
<213> ORGANISM: Homo sapiens

<400> SEQUENCE: 16

Cys Gly Pro Gly Arg Gly Phe Lys Arg His Pro Lys Lys
 1               5                  10                  15

Leu Thr Pro Leu Ala Tyr Lys Gln Phe Ile Pro Asn Val Ala Glu
                20                  25                  30

Lys Thr Leu Gly Ala Ser Gly Arg Tyr Glu Gly Lys Ile Ser Arg

-continued

```
                35                  40                  45
Asn Ser Glu Arg Phe Lys Glu Leu Thr Pro Asn Tyr Asn Pro Asp
             50                  55                  60
Ile Ile Phe Lys Asp Glu Glu Asn Thr Gly Ala Asp Arg Leu Met
         65                  70                  75
Thr Gln Arg Cys Lys Asp Lys Leu Asn Ala Leu Ala Ile Ser Val
     80                  85                  90
Met Asn Gln Trp Pro Gly Val Lys Leu Arg Val Thr Glu Gly Trp
 95                 100                 105
Asp Glu Asp Gly His His Ser Glu Glu Ser Leu His Tyr Glu Gly
             110                 115                 120
Arg Ala Val Asp Ile Thr Thr Ser Asp Arg Asp Arg Ser Lys Tyr
         125                 130                 135
Gly Met Leu Ala Arg Leu Ala Val Glu Ala Gly Phe Asp Trp Val
     140                 145                 150
Tyr Tyr Glu Ser Lys Ala His Ile His Cys Ser Val Lys Ala Glu
 155                 160                 165
Asn Ser Val Ala Ala Lys Ser Gly Gly
             170

<210> SEQ ID NO 17
<211> LENGTH: 175
<212> TYPE: PRT
<213> ORGANISM: Homo sapiens

<400> SEQUENCE: 17

Cys Gly Pro Gly Arg Val Val Gly Ser Arg Arg Arg Pro Pro Arg
 1               5                  10                  15
Lys Leu Val Pro Leu Ala Tyr Lys Gln Phe Ser Pro Asn Val Pro
             20                  25                  30
Glu Lys Thr Leu Gly Ala Ser Gly Arg Tyr Glu Gly Lys Ile Ala
         35                  40                  45
Arg Ser Ser Glu Arg Phe Lys Glu Leu Thr Pro Asn Tyr Asn Pro
     50                  55                  60
Asp Ile Ile Phe Lys Asp Glu Glu Asn Thr Gly Ala Asp Arg Leu
 65                  70                  75
Met Thr Gln Arg Cys Lys Asp Arg Leu Asn Ser Leu Ala Ile Ser
             80                  85                  90
Val Met Asn Gln Trp Pro Gly Val Lys Leu Arg Val Thr Glu Gly
         95                 100                 105
Trp Asp Glu Asp Gly His His Ser Glu Glu Ser Leu His Tyr Glu
    110                 115                 120
Gly Arg Ala Val Asp Ile Thr Thr Ser Asp Arg Asp Arg Asn Lys
    125                 130                 135
Tyr Gly Leu Leu Ala Arg Leu Ala Val Glu Ala Gly Phe Asp Trp
    140                 145                 150
Val Tyr Tyr Glu Ser Lys Ala His Val His Cys Ser Val Lys Ser
    155                 160                 165
Glu His Ser Ala Ala Ala Lys Thr Gly Gly
    170                 175

<210> SEQ ID NO 18
<211> LENGTH: 176
<212> TYPE: PRT
<213> ORGANISM: Homo sapiens

<400> SEQUENCE: 18
```

-continued

```
Cys Gly Pro Gly Arg Gly Pro Val Gly Arg Arg Tyr Ala Arg
 1               5                  10                  15

Lys Gln Leu Val Pro Leu Leu Tyr Lys Gln Phe Val Pro Gly Val
                20                  25                  30

Pro Glu Arg Thr Leu Gly Ala Ser Gly Pro Ala Glu Gly Arg Val
                35                  40                  45

Ala Arg Gly Ser Glu Arg Phe Arg Asp Leu Val Pro Asn Tyr Asn
                50                  55                  60

Pro Asp Ile Ile Phe Lys Asp Glu Glu Asn Ser Gly Ala Asp Arg
                65                  70                  75

Leu Met Thr Glu Arg Cys Lys Glu Arg Val Asn Ala Leu Ala Ile
                80                  85                  90

Ala Val Met Asn Met Trp Pro Gly Val Arg Leu Arg Val Thr Glu
                95                  100                 105

Gly Trp Asp Glu Asp Gly His His Ala Gln Asp Ser Leu His Tyr
                110                 115                 120

Glu Gly Arg Ala Leu Asp Ile Thr Thr Ser Asp Arg Asp Arg Asn
                125                 130                 135

Lys Tyr Gly Leu Leu Ala Arg Leu Ala Val Glu Ala Gly Phe Asp
                140                 145                 150

Trp Val Tyr Tyr Glu Ser Arg Asn His Val His Val Ser Val Lys
                155                 160                 165

Ala Asp Asn Ser Leu Ala Val Arg Ala Gly Gly
                170                 175
```

ANTI-HEDGEHOG ANTIBODIES

CROSS REFERENCE TO RELATED APPLICATIONS

This application is a continuation application of U.S. Ser. No. 13/217,191, filed Aug. 24, 2011, now abandoned, which is a divisional application of application Ser. No. 12/341,910, now U.S. Pat. No. 8,030,454, filed Dec. 22, 2008, which claimed the benefit of priority to U.S. provisional application No. 61/017,232, filed Dec. 28, 2007, and U.S. provisional application No. 61/099,864, filed Sep. 24, 2008, the disclosures of which are all incorporated herein by reference in their entirety.

FIELD OF THE INVENTION

The present invention relates generally to methods of diagnosing cancer and detecting protein expression in tumors. More specifically, the invention relates to antibodies that bind to mammalian hedgehog, and to their use in diagnosis and treatment of conditions characterized by hedgehog expression, including cancer.

BACKGROUND OF THE INVENTION

Members of the hedgehog family of signaling molecules mediate many important short- and longrange patterning processes during invertebrate and vertebrate embryonic, fetal, and adult development. In *Drosophila melanogaster*, a single hedgehog gene regulates segmental and imaginal disc patterning. In contrast, in vertebrates, a hedgehog gene family (e.g., in mammals, Shh, Dhh, Ihh, collectively "Hh") is involved in the control of proliferation, differentiation, migration, and survival of cells and tissues derived from all three germ layers, including, e.g., left-right asymmetry, CNS development, somites and limb patterning, chondrogenesis, skeletogenesis and spermogenesis.

Hedgehog signaling occurs through the interaction of hedgehog protein with the hedgehog receptor, Patched (Ptch), and the co-receptor Smoothened (Smo). There are two mammalian homologs of Ptch, Ptch-1 and Ptch-2 ("collectively "Ptch"), both of which are 12 transmembrane proteins containing a sterol sensing domain (Motoyama et al., *Nature Genetics* 18: 104-106 (1998), Carpenter et al., *P.N.A.S. (U.S.A.)* 95 (23): 13630-40 (1998). The interaction of Hh with Ptch triggers a signaling cascade that results in the regulation of transcription by zinc-finger transcriptions factors of the Gli family.

Malignant tumors (cancers) are the second leading cause of death in the United States, after heart disease (Boring et al., *CA Cancel J. Clin.* 43:7 (1993)). Cancer features one of more of the following characteristics: (1) an the increase in the number of abnormal, or neoplastic, cells derived from a normal tissue which proliferate to form a tumor mass, (2) the invasion of adjacent tissues by these neoplastic tumor cells, and (3) the generation of malignant cells which eventually spread via the blood or lymphatic system to regional lymph nodes and to distant sites via a process called metastasis. In a cancerous state, a cell proliferates under conditions in which normal cells would not grow. Cancer manifests itself in a wide variety of forms, characterized by different degrees of invasiveness and aggressiveness.

As often is the case when pathways that are active during embryogenic development and mostly inactive in adults, reactivation of hedgehog signaling has been implicated in a wide variety of cancers and carcinogenesis. The earliest examples of Hh signaling in cancers came from the discovery that Gorlin's syndrome, in which patients frequently suffer basal cell carcinomas and are also predisposed to medulloblastomas and rhabdomyosarcomas, is due to an inactivating mutation in Ptch, resulting in Hh pathway activation (Hahn et al 1998 Cell 85 p841; Johnson et al 1996, Science 272 p1668). Subsequently inactivating mutations in Ptch (~90%) and or activating mutations in Smo (~10%) were found to be responsible for sporadic basal cell carcinomas (Xie et al 1998, Nature 391 p90).

Recently, it has become clear that another class of Hh-associated cancers exist, which depend on Hh ligand secretion from the tumor rather than mutational activation for pathway activation. Such cancers include prostate, pancreatic and small cell lung cancers (Watkins et al 2003, Nature 422 p313; Thayer et al 2003 Nature 425 p851; Berman et al 2003 Nature 425 p846). A subset of such cancers can be treated by Hh antagonists such as small molecule antagonists of Smo or anti-Hh antibody 5E1 (Chen et al 2002, PNAS 99 p14071; Williams et al 2003 PNAS 100 p4616; Rubin and de Sauvage 2006 Nature Reviews Drug Discovery 5 p1026). While not all Hh-expressing tumors respond to such antagonists, it is very likely that those that do not express Hh will not respond; indeed the Hh-negative DLD-1 colorectal xenograft model is not inhibited by such treatment under conditions where Hh-positive LS180, HT29 and HT55 tumor models are (Yauch/de Sauvage et al. January 2008). As a result, there is a need for an effective technique for determining hedgehog expression prior to application of the hedgehog antagonists so as to identify hedgehog-secreting tumors, in order to maximize the overall response rate.

Currently available antibodies that bind to mammalian hedgehog (e.g., H160, Santa Cruz Biotech) are ineffective reagents to detect the presence of hedgehog signaling because they do not show sufficient sensitivity in the absence of background staining This is particularly true on FFPE (formalin-fixed paraffin-embedded) tissue specimens.

As a result, there is a need for antibodies that bind to mammalian hedgehog (e.g., sonic hedgehog, Indian hedgehog and desert hedgehog), particularly in FFPE specimens, for use to detecting the expression of hedgehog both in diagnostic assays and treatment regimens.

SUMMARY OF THE INVENTION

The invention provides for anti-hedgehog antibodies, and their use in the detection of hedgehog expression and the treatment of including hedgehog responsive cancer.

In one embodiment, the invention relates to an anti-hedgehog antibody comprising a heavy chain and a light chain, wherein the heavy chain comprises: HCFR1-HCHVR1-HCFR2-HCHVR2-HCFR3-HCHVR3-HCFR4-CR and the light chain comprises: LCFR1-LCCDR1-LCFR2-LCCDR2-LCFR3-LCCDR3-LCFR4. In a specific aspect, the anti-Hh antibody comprises the heavy and light chain sequences of 95.9.

In another embodiment, the invention relates to a method of detecting hedgehog expression in tissue comprising contacting said tissue with an anti-hedgehog antibody and measuring the extent of binding, wherein said anti-hedgehog antibody binds to hedgehog polypeptide at an epitope within the region of amino acid residues 75-96. In a specific aspect, the tissue is a tumor or cancer. In yet another specific aspect, the tissue is removed from the host prior to the determination. In a further specific aspect, the tissue sample is FFPE prior the contacting with the anti-Hh antibody. In a further specific aspect, the determination method is selected from the group consisting of: of IHC and Western blot. In a specific aspect, the binding sensitivity is greater than that of the anti-Hh antibody H160. In a further specific aspect, the anti-Hh antibody does not compete with ptch for binding to Shh. In a further specific aspect, the anti-Hh is selected from the group consisting of 95.3, 95.7 and 95.9.

In yet another embodiment, the invention relates to a method for identifying tumors responsive to hedgehog antagonists, comprising contacting the tumor tissue or tissue proximal to the tumor with an anti-hedgehog antibody wherein said anti-hedgehog antibody binds to hedgehog polypeptide at an epitope within the region of amino acid residues 75-96 and determining if hedgehog is overexpressed in said tissue, compared to normal tissue. In a specific aspect, the tissue is removed from the host prior to the determination. In yet another specific aspect, the tissue sample is FFPE prior the contacting with the anti-Hh antibody. In a further specific aspect, the determination method is selected from the group consisting of: of IHC and Western blot. In a specific aspect, the binding sensitivity is greater than that of the anti-Hh antibody H160. In a further specific aspect, the anti-Hh antibody does not compete with ptch for binding to Shh. In a further specific aspect, the anti-Hh is selected from the group consisting of 95.3, 95.7 and 95.9.

In a further embodiment, the invention relates to a cancer treatment regimen in a patient comprising:

(a) contacting a tumor and/or tissue proximal to the tumor removed from the patient with an anti-hedgehog antibody wherein said anti-hedgehog antibody binds to hedgehog polypeptide at an epitope within the region of amino acid residues 75-96, (b) detecting the presence of hedgehog expression, (c) comparing the hedgehog expression with that of normal or tissue of the same type or origin not associated with the tumor, and if such hedgehog is overexpressed, (d) treating the patient with a hedgehog antagonist.

In a specific aspect, the tissue is removed from the host prior to the determination. In another specific aspect, the tissue sample is FFPE prior the contacting with the anti-Hh antibody. In yet another specific aspect, the determination method is selected from the group consisting of: of IHC and Western blot. In a further specific aspect, the binding sensitivity is greater than that of the anti-Hh antibody H160. In a further specific aspect, the anti-Hh antibody does not compete with ptch for binding to Shh. In a further specific aspect, the anti-Hh antibody is selected from the group consisting of 95.3, 95.7 and 95.9.

In a further embodiment, the invention relates to an article of manufacture (kit) for measuring hedgehog expression comprising an anti-hedgehog antibody wherein said anti-hedgehog antibody binds to hedgehog polypeptide at an epitope within the region of amino acid residues 75-96, and instructions for determining if hedgehog is overexpressed in a tissue, comprising contacting such tissue with such anti-hedgehog antibody and measuring the extent of binding. In a specific aspect, the tissue is a tumor or cancer. In yet another specific aspect, the tissue is removed from the host prior to the determination. In a further specific aspect, the tissue sample is FFPE prior the contacting with the anti-Hh antibody. In a further specific aspect, the determination method is selected from the group consisting of: of IHC and Western blot. In a specific aspect, the binding sensitivity is greater than that of the anti-Hh antibody H160. In a further specific aspect, the anti-Hh antibody does not compete with ptch for binding to Shh. In a further specific aspect, the anti-Hh antibody is selected from the group consisting of 95.3, 95.7 and 95.9.

In a further embodiment, the invention relates to a method of screening patients with abnormal tissue growth for the risk of developing cancer, comprising determining if such tissue overexpresses hedgehog signaling with a hedgehog antibody wherein said anti-hedgehog antibody binds to hedgehog polypeptide at an epitope within the region of amino acid residues 75-96, comprising contacting such tissue with such anti-hedgehog antibody and measuring the extent of binding. In a specific aspect, the tissue is a tumor or cancer. In yet another specific aspect, the tissue is removed from the host prior to the determination. In a further specific aspect, the tissue sample is FFPE prior the contacting with the anti-Hh antibody. In a specific aspect, the binding sensitivity is greater than that of the anti-Hh antibody H160. In a further specific aspect, the anti-Hh antibody does not compete with ptch for binding to Shh. In a further specific aspect, the anti-Hh antibody is selected from the group consisting of 95.3, 95.7 and 95.9. In a further specific aspect, the determination method is selected from the group consisting of IHC and Western Blot.

In a further embodiment, the invention relates to a method of treating cancer comprising (a) contacting tissue suspected of being cancerous or tissue proximal to such tissue with an anti-hedgehog antibody wherein said anti-hedgehog antibody binds to hedgehog polypeptide at an epitope within the region of amino acid residues 75-96; (b) determining if hedgehog is overexpressed; and (c) treating with a hedgehog antagonist. In yet another specific aspect, the tissue is removed from the host prior to the determination. In a further specific aspect, the tissue sample is FFPE prior to contacting with the anti-Hh antibody. In a specific aspect, the determination method is selected from the group consisting of IHC and Western blot. In a specific aspect, the binding sensitivity of the anti-hedgehog antibody is greater than that of the anti-Hh antibody H160. In a further specific aspect, the anti-Hh antibody does not compete with ptch for binding to Shh. In a further specific aspect, the anti-Hh antibody is selected from the group consisting of 95.3, 95.7 and 95.9.

DESCRIPTION OF THE FIGURES

FIG. 3A shows micrographs demonstrating monoclonal antibodies 95.9, 95.7 and 95.3 also cross react with Ihh and Dhh. COS cells transfected with full length human Shh (top row), Ihh (middle row) and Dhh (bottom row) were processed for immunofluorescence as in FIG. 1, using affinity purified 95.3 (1-3) 95.7 (4-6), 95.9 (7-9) or H-160 (10-12) antibodies. Scale bar=30 µm. FIG. 3B is a Western blot of 293 cells either untransfected (WT) or transfected with human Dhh, Ihh or Shh full length proteins as indicated and immunolabeled with 5 mg/ml purified 95.9 rMab (upper panel) or H-160 (lower panel). Both antibodies recognize all three full length (FL) Hh proteins (≈50 kDa) as well as the secreted Hh-N termini 22 kDa), although 95.9 did not recognize the ≈98 kDa background band that H-160 labeled in untransfected cells. Molecular weight markers in kDa are shown on the left.

FIGS. 4A and B show the N-terminal sequences of 95.9, 95.7 and 95.3. This strongly suggests that they are likely identical subclones. FIG. 4A depicts the N-terminal sequences of the light chains of the three supposedly identical subclones of 95 are indeed identical in positions where the sequence was unambiguous. The amino acid residues in parentheses indicate ambiguous amino acids, dashes indicate positions for which an amino acid was not determinable, italic letters indicate discrepancies between the obtained N-terminal sequence and the actual cloned sequence of 95.9 determined by DNA sequencing and conceptual translation ($2^{nd}$ row). Amino acid position numbers (numbered with the missing signal sequence starting at 1) are indicated in the top row of the table. FIG. 4B depicts the N-terminal sequences of the 95 subclone heavy chains were complicated by the presence of endogenous myeloma cell heavy chain, thus two (partially mixed) sequences are shown for each subclone. The presence of glutamine at position 20 is inferred.

FIG. 5 shows that 95.9 epitope maps to amino acids 76-90 within residues 24 to 197 of human sonic hedgehog (SEQ ID NO: 16). 95.9 coupled to agarose beads was incubated with recombinant Shh and then subjected to trypsin digestion. The peptide was protected from trypsin by 95.9 binding was eluted, identified by mass spectrometry and confirmed by amino acid sequencing as amino acids 76-90, a region of Shh that is identical to residues 76-90 within residues 24 to 197 of Ihh (SEQ ID NO: 17) and contains 3 amino acid residues different to Dhh (SEQ ID NO: 18) (box region in the alignment of the 3 Hh —N-terminal ligands, numbered with the first amino acid residue of the signal sequence (not shown) designated as 1.

FIGS. 7A-E show that IHC staining by anti-Hh Ab 95.9 correlates well with transcript levels of Shh. 36 human colon cancer cell lines were subjected to Q-PCR analysis of Shh mRNA and IHC analysis (FFPE) using the purified 95.9 anti-Hh rMab in parallel. Upper panel shows images of representative cell pellets falling into each of the four IHC scoring categories as follows: A) Hh-negative cell line, IHC score 0+, although some non-specific nuclear staining is discernible; B) IHC score 1+ (weak staining), C) cells illustrating 2+IHC score (moderate staining), D) cells showing strong staining (3+IHC score). Scale bar is 50 µm. FIG. 6E shows that relative Shh mRNA levels (Delta Ct values from Q-PCR analysis) in each IHC score group, illustrating the trend towards stronger 95.9 staining with lower Ct values (higher mRNA levels). The Spearman coefficient of this correlation is −0.160, which is statistically significant (p=0.0001).

FIGS. 9A-B show that IHC staining of tumor TMA by anti-Hh Ab 95.9 detects different levels of Hh expression in colon, ovarian and pancreatic tumors, respectively. Greater than 80% of CRC, OvCa and PancCa express Hh ligands. A) Representative Hh-negative (0+), low (1+), medium (2+) and high (3+) images are shown for colon (top row), ovarian (middle row) and pancreatic (bottom row) tumors from arrays of normal and tumor samples stained with the 95.9 antibody. B) The total number of samples (n) stained is indicated for each tumor type, and the number and percentages of the total examined are indicated for 95.9 staining falling into each expression level category.

FIGS. 11A-B show the 95.9 amino acid sequences. The cloned DNAs encoding 95.9's mature region heavy chain (A) or light chain (B) (including Fc domain) was fused in frame with a generic antibody signal sequence (box) and translated.

FIG. 12 shows Immunohistochemistry using mAb 95.5 and mAb H-160 on mouse embryo E 10.5 neural tube, normal ovary (ISH−) and ovarian cancer tissue (ISH+).

DETAILED DESCRIPTION OF THE INVENTION

I. Definitions

Figure 1:
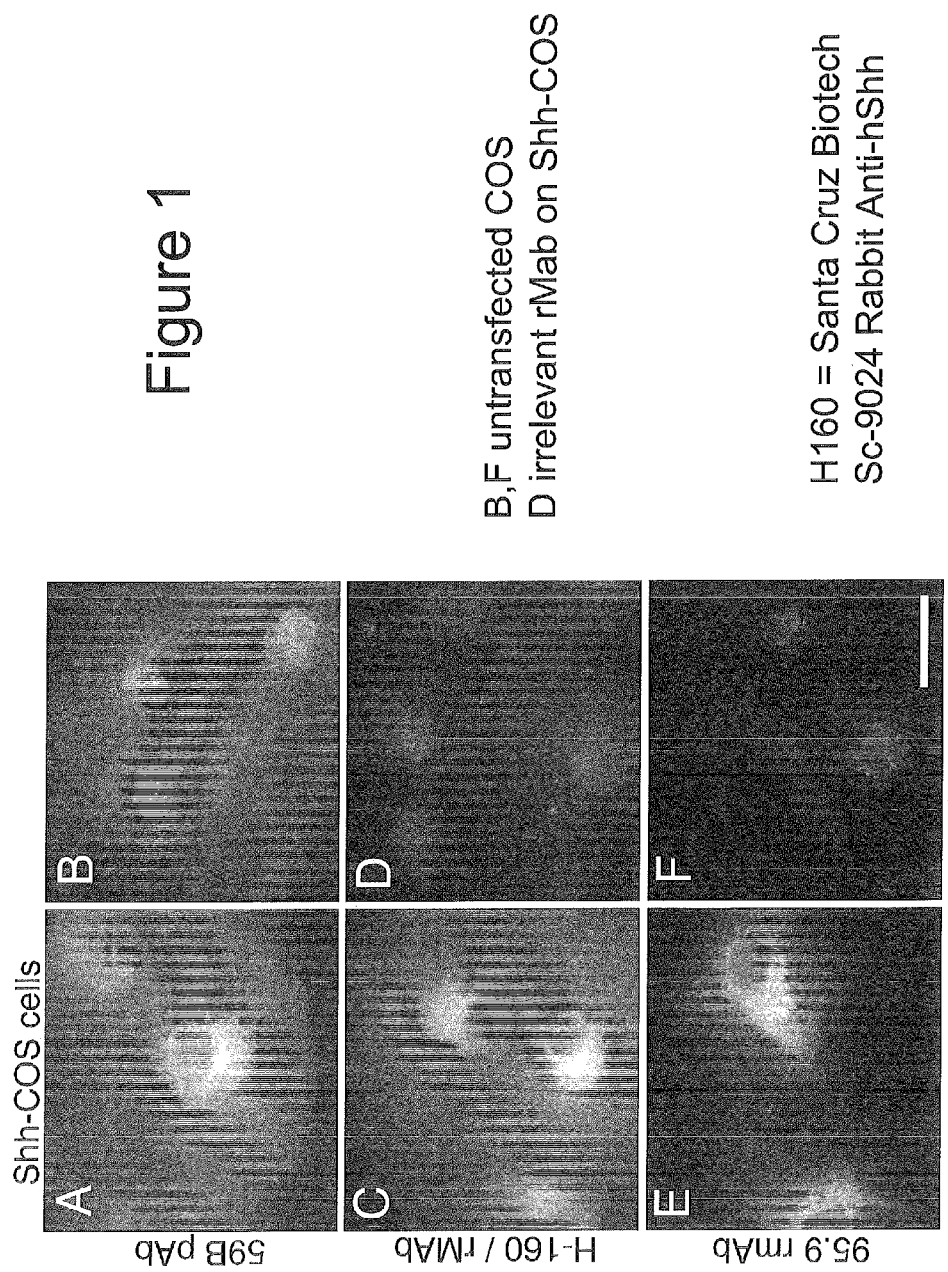
FIGS. 1A-F are micrographs showing the binding of parent polyclonal anti-Shh antibody ("59 pAb") and its derived monoclonal rMab specifically recognize Shh-transfected COS cells by immunofluorescence (IF). Cos-7 cells with or without stably transfected human Shh were fixed, permeabilized and stained with rabbit antibodies, detected with Cy3-conjugated anti-human and examined by fluorescence microscopy. 59A+B polyclonal on Shh-COS (A) or untransfected (B) cells; C)H-160 on Shh-COS cells; D) irrelevant rmAb on Shh-COS cells; purified 95.9 rMab on Shh-COS (E) and untransfected (F) cells. Scale bar is 30 µm.

"FFPE" means formalin fixed, paraffin embedded, which is tissue resulting from a dissection or biopsy, that is then fixed in order to prevent degeneration and to allow for histological, pathological or cytological studies. This fixed tissue is then embedded in the wax to cut its fine sections and then, to stain it with Hemotoxylin and Eosin Stain, after which microtoming is performed by cutting into fine sections. Fixation is the process by which the tissue is immobilized, killed and preserved for further study. Fixation makes tissue permeable to staining reagents and cross-links its macromolecules so that they are stabilized and locked in position. Any suitable fixatives may be used for this purpose, and include for example, bouine solution, formaline, or liquid nitrogen.

A "hedgehog responsive cancer" is a cancer or tumor that is mediated by, or associated with hedgehog signaling such that the presence of hedgehog (i.e., sonic hedgehog, indian hedgehog and/or desert hedgehog) is necessary or essential for the survival and/or progression of the cancer or tumor. Such hedgehog can be autocrine (i.e., produced by the tumor itself) or paracrine, in which hedgehog is produced by tissues in the proximity of the tumor or cancer. In a specific aspect, a "hedgehog responsive cancer" is one that is treated upon the application of a hedgehog antagonist.

The "overexpression" of hedgehog in a particular tissue or tumor refers to hedgehog, such as polypeptide and/or nucleic acid encoding such polypeptide, that is expressed at a level higher than that which is present for non-diseased tissue of the same tissue type or origin, or which is in the proximity of a tumor or cancer that is a hedgehog responsive cancer, and is expressing hedgehog at a higher level as compared with that which is expressed when a hedgehog responsive cancer is not present, such as in a healthy, or non-diseased state. Such overexpression may be caused by gene amplification or by increased transcription or translation. Hedgehog overexpression may be determined in a diagnostic or prognostic assay by evaluating increased levels of the hedgehog protein present on the surface of a cell, or secreted by the cell (e.g., via an immunohistochemistry assay using the anti-hedgehog antibodies of the invention. Alternatively, or additionally, one may measure levels of hedgehog polypeptide-encoding nucleic acid or mRNA in the cell, e.g., via fluorescent in situ hybridization using a nucleic acid based probe corresponding to a hedgehog-encoding nucleic acid or the complement thereof; (FISH; see WO98/45479 published October, 1998), Southern blotting, Northern blotting, or polymerase chain reaction (PCR) techniques, such as real time quantitative PCR (RT-PCR). One may also study hedgehog polypeptide overexpression by measuring shed antigen in a biological fluid such as serum, e.g, using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., J. Immunol. Methods 132:73-80 (1990)). Aside from the above assays, various in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

A "hedgehog antagonist" is an antibody, antigen binding fragment thereof, other biological molecule or small molecule that antagonizes or blocks hedgehog signaling, either by directly binding to a hedgehog signaling pathway component and thereby blocking the signal transduction through such component a component, or by preventing the binding of a hedgehog signaling pathway component to its natural binding partner so as to prevent the transduction of a hedgehog signal.

The terms "hedgehog signaling pathway", "hedgehog pathway" and "hedgehog signal transduction pathway" as used herein, interchangeably refer to the signaling cascade mediated by hedgehog and its receptors (e.g., patched, patched-2) and which results in changes of gene expression and other phenotypic changes typical of hedgehog activity. The hedgehog pathway may be activated in the absence of hedgehog through activation of a downstream component (e.g., overexpression of Smoothened or transfections with Smoothened or Patched mutants to result in constitutive activation with activate hedgehog signaling in the absence of hedgehog). The transcription factors of the Gli family are often used as markers or indicators of hedgehog pathway activation.

The term "Hh signaling component" refers to gene products that participate in the Hh signaling pathway. An Hh signaling component frequently materially or substantially affects the transmission of the Hh signal in cells or tissues, thereby affecting the downstream gene expression levels and/or other phenotypic changes associated with hedgehog pathway activation.

Each Hh signaling component, depending on their biological function and effects on the final outcome of the downstream gene activation or expression, can be classified as either positive or negative regulators. A positive regulator is an Hh signaling component that positively affects the transmission of the Hh signal, i.e., stimulates downstream biological events when Hh is present. A negative regulator is an Hh signaling component that negative affects the transmission of the Hh signal, i.e. inhibits downstream biological events when Hh is present.

The binding of Hh to Ptch releases Smoothened (Smo), a 7 transmembrane G-coupled protein to then activate an intricate intracellular signal-transduction pathway. The activation of Smo then leads to signaling through a multimolecular complex, including Costal2 (Cos2), Fused (Fu) and suppressor of Fused (Su(Fu)), resulting in nuclear transport of the transcription factor Gli. Ho et al., Curr. Opin. Neurobiol. 12:57-63 (2002); Nybakken et al., Curr. Opin. Genet. Dev. 12: 503-511 (2002); i Altaba et al., Nat. Rev. Neurosci. 3: 24-33 (2002). There are three known Gli transcription factors in verebrates: Gli1, Gli2 and Gli3. While Gli1 is a transcriptional activator that is universally induced in Hh-responsive cells, Gli2 and Gli3 can act either as activators or repressors of transcription depending on the cellular context. Absent Hh signaling, Gli3 is processed into a smaller, nuclear transcriptional repressor that lacks the carboxy-terminal domain of full-length Gli3. Upon activation of Smo, Gli3 protein cleavage is prevented, and the full-length form with transcription-activation function is generated. Gli2 also encodes a repressor function in its carboxy-terminally truncated form, but its formation does not appear to be regulated by Hh signaling. Stecca et al., J. Biol. 1(2):9 (2002).

Standard Definitions:

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antagonist" is used in the broadest sense, and includes any molecule that partially or fully blocks, inhibits, or neutralizes a biological activity of a hedgehog signaling or a hedgehog signaling pathway component. Suitable hedgehog antagonist antagonist molecules specifically include agonist or antagonist antibodies or antibody fragments, fragments or amino acid sequence variants of native hedgehog polypeptides, peptides, antisense oligonucleotides, small organic molecules, etc. Methods for identifying hedgehog antagonists may comprise contacting a cell in which hedgehog signaling is active with a candidate antagonist molecule and measuring a detectable change in one or more biological activities normally associated with hedgehog signaling (E.g., nuclear Gli expression).

"Treating" or "treatment" or "alleviation" refers to both therapeutic treatment and prophylactic or preventative measures, wherein the object is to prevent or slow down (lessen) the targeted pathologic condition or disorder. A subject or mammal is successfully "treated" for a hedgehog responsive cancer if, after receiving a therapeutic amount of a hedgehog antagonist, the patient shows observable and/or measurable reduction in, or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of the treatment of, alleviating the symptoms of or diagnosis of a cancer refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

An "effective amount" of a hedgehog antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of a hedgehog antagonist effective to "treat" a disease or disorder in a subject or mammal. In the case of cancer, especially a hedgehog responsive cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

The term "package insert" is used to refer to instructions customarily included in commercial packages of therapeutic products that contain information about the indications, usage, dosage, administration, contraindications and/or warnings concerning the use of such therapeutic products.

Antibody Definitions:

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, $F(ab')_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., Basic and Clinical Immunology, 8th Edition, Daniel P. Sties, Abba I. Terr and Tristram G. Parsolw (eds), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2, IgG3, IgG4, IgA1 and IgA2.

An "isolated" antibody is one that has been identified, separated and/or recovered from a component of its production environment (e.g., naturally or recombinantly). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., Sequences of Immunological Interest, Fifth Edition, National Institute of Health, Bethesda, Md. (1991)). The constant domains are not involved directly in the binding of antibody to an antigen, but exhibit various effector functions, such as participation of the antibody in antibodydependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., Nature, 256: 495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., Protein Eng. 8(10): 1057-1062 [1995]); single-chain antibody molecules and multispecific antibodies formed from antibody fragments.

Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigenbinding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains 5 held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in The Pharmacology of Monoclonal Antibodies, vol. 113, Rosenburg and Moore eds., Springer-Verlag, New York, pp. 269-315 20 (1994).

The term "hypervariable region," "HVR," or "HV," when used herein refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. Immunity 13:37-45 (2000); Johnson and Wu in Methods in Molecular Biology 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., Nature 363:446-448 (1993) and Sheriff et al., Nature Struct. Biol. 3:733-736 (1996).

A number of HVR delineations are in use and are encompassed herein. The HVRs that are Kabat complementarity-determining regions (CDRs) are based on sequence variability and are the most commonly used (Kabat et al., supra). Chothia refers instead to the location of the structural loops (Chothia and Lesk J. Mol. Biol. 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et agl., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

An "acceptor human framework" for the purposes herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

Alternatively, the framework and HVR definitions of the anti-Hh antibody of the inventions may be defined as follows: (a) the heavy chain may comprise: HCFR1-HCHVR1-HCFR2-HCHVR2-HCFR3-HCHVR3-HCFR4-CR; wherein HCFR1=QSVKESGGGLVQPEGSLTLTCTVS (SEQ ID NO: 1), HCHVR1=GFSLSSYDMS (SEQ ID NO: 2 XM), HCFR2=WVRQAPGSGLEWI (SEQ ID NO: 3), HCHVR2=GGILSGGSAYYASWAKS (SEQ ID NO: 4), HCFR3=RSTITKNTNLNTVTLKMTSLTAADTATYFC (SEQ ID NO: 5), HCHVR3=ARGIYPVGTNYNI (SEQ ID NO: 6), HCFR4=WGPGTLVTVSSG (SEQ ID NO: 7), CR=QPKAPSVFPLAPCCGDTPSSTVTLGCLVKGYL-PEPVTVTWNSGTLTNGVRTFPSV RQSSGLYSLSSV-VSVTSSSQPVTCNVAHPATNTKVDK-
TVAPSTCSKPTCPPPELLG GPSVFIFPPKPKDTLMIS-RTPEVTCVVVDVSQDDPEVQFTWYINNEQVRTAR-PPLR EQQFNSTIRVVSTLPIAHQDWL-RGKEFKCKVHNKALPAPIEKTISKARGQPLEPKV YTMGPPREELSSRSVSLTCMINGFYPS-DISVEWEKNGKAEDN5 YKTTPAVLDSDGSYFLY-SKLSVPTSEWQRGDVFTCSVMHEALH-NHYTQKSISRSP GK (SEQ ID NO: 8).

(b) the light chain may comprise: LCFR1-LCCDR1-LCFR2-LCCDR2-LCFR3-LCCDR3-LCFR4; wherein LCFR1=DIAVLTQTPSPVSAAVGGTVTINC (SEQ ID NO: 9), LCHVR1=QSSPSVYSNYLA (SEQ ID NO: 10), LCFR2=WYQQKPGQPPKLLI (SEQ ID NO: 11), LCHVR2=YYASTLAS (SEQ ID NO: 12), LCFR3=GVPSRFKGSGSGTEFTLTISDLECADAATYYC (SEQ ID NO: 13), LCHVR3=AGGYIDTSDTA (SEQ ID NO: 14), LCFR4=FGGGTEVVVKGDPVAPTVLIFPPAADQVAT-GTVTIVCVANKYFPDVTVTWEVDG TTQTTGIENSKT-

PQNSADCTYNLSSTLTLTSTQYNSH-KEYTCKVTQGTTSVVQSFN RGDC (SEQ ID NO: 15).

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., Bio/Technology 10:779-783 (1992) describes affinity maturation by VH- and VL-domain shuffling. Random mutagenesis of HVR and/or framework residues is described by, for example: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154 (7):3310-9 (1995); and Hawkins et al, J. Mol. Biol. 226:889-896 (1992).

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. For example, the anti-Hh antibodies of the present invention specifically bind to Hh (e.g., human sonic hedgehog (shh), human indian hedgehog (ihh) or human desert hedgehog (dhh) and not to any other polypeptide.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen. The anti-hedgehog antibodies of the present invention are not blocking in the sense that once bound to hedgehog, they do not prevent the binding of hedgehog so bound to patched.

The term "solid phase" describes a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

The term "Fc region" herein is used to define a C-terminal region of an immunoglobulin heavy chain, including native-sequence Fc regions and variant Fc regions. Suitable native-sequence Fc regions for use in the antibodies of the invention include human IgG1, IgG2, IgG3 and IgG4.

II. Hedgehog Antagonist Methods

Because hedgehog expression has been associated with multiple physiological conditions and disease states, including cancers that would be responsive to hedgehog antagonists, the anti-hedgehog antibodies of the present invention are useful to detect such events and disease states, as well as to identify such responsive cancers.

A. Angiogenesis

Since hedgehog is known to stimulate angiogenesis, it is expected that hedgehog antagonists, which inhibit hedgehog activity, would be expected to inhibit angiogenesis, particularly when some level of hedgehog signaling is a necessary perquisite for angiogenesis. The anti-hedgehog antibodies of the invention can be used to specifically identify tissues or conditions when hedgehog expression is associated with angiogenesis.

Angiogenesis is fundamental to many disorders. Persistent, unregulated angiogenesis occurs in a range of disease states, tumor metasteses and abnormal growths by endothelial cells. The vasculature created as a result of angiogenic processes supports the pathological damage seen in these diseases.

Diseases associated with or resulting from angiogenesis include: tumor growth, tumor metastasis or abnormal growths by endothelial cells, including neovascular disease, age-related macular degeneration, diabetic retinopathy, retinopathy of prematurity, corneal graft rejection, neovascular glaucoma, retrolental fibroplasias, epidemic keratoconjuctivitis, Vitamin A deficiency, contact lens overwear, atopic keratitis, superior limbic keratitis, pterygium keratitis sicca, Sjogren's syndrome, acne rosacea, phylctenulosis, syphilis, mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, marginal keratolysis, rheumatoid arthritis, systemic lupus, polyarteritis, trauma, Wegener's granulomatosis, sacroidosis, scleritis, Stevens-Johnson syndrome, pemphigoid radial keratotomy, corneal graph rejection, rheumatoid arthritis, systemic lupus, polyarteritis, trauma, Wegener's granulomatosis, sarcoidosis, scleritis, Stevens-Johnson syndrome, pemphigoid radial keratotomy, corneal graph rejection, rheumatoid arthritis, osteoarthritis chronic inflammation (e.g., ulcerative colitis or Crohn's disease), hemangioma, Osler-Weber Rendu disease, and hereditary hemorrhagic telangiectasis.

Angiogenesis plays a critical role in cancer. A tumor cannot expand without a blood supply to provide nutrients and remove cellular wastes. Tumors in which angiogenesis is important include solid tumors such as rhabdomyosarcomas, retinoblastoma, Ewing sarcoma, neuroblastoma, osteosarcoma, and benign tumors such as acoustic neuroma, neurofibroma, trachoma and pyogenic granulomas. Angiogenic factors have been found associated with several solid tumors, and preventing angiogenesis could halt the growth of these tumors and the resultant damage to the animal due to the presence of the tumor. Angiogenesis is also associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

In addition to tumor growth, angiogenesis is important in metastasis. Initially, angiogenesis is important in the vascularization of the tumor which allows cancerous cells to enter the blood stream and to circulate throughout the body. After the tumor cells have left the primary site, and have settled into the secondary, metastatic site, angiogenesis must occur before the new tumor can grow and expand. Therefore, prevention of angiogenesis could lead to the prevention of metastasis of tumors and possibly contain the neoplastic growth at the primary site.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

B. Disorders Resulting from Hyperactive Hedgehog Signaling

The anti-hedgehog antibodies of the invention may be used to determine is specific tissue and/or cells exhibit hedgehog overexpression. This may occur in combination with other measurement of hedgehog pathway activation, such as through the measurement of expression of gli genes activated by the hedgehog signaling pathway. Gli-1, gli-2 and gli-3, most consistently correlate with hedgehog signaling across a wide range or tissues and disorders, while gli-3 is somewhat less so. The gli genes encode transcription factors that activate expression of many genes needed to elicit the full effects of hedgehog signaling. However, the Gli-3 transcription factors can also act as a repressor of hedgehog effector genes, and therefore, expression of gli-3 can cause a decreased effect of the hedgehog signaling pathway. Whether gli-3 acts as a transcriptional activator or repressor depends on post-translational events, and therefore it is expected that methods for detecting the activating form (versus the repressing form) of Gli-3 protein would also be a reliable measure of hedgehog pathway activation. The gli-1 gene is strongly expressed in a wide array of cancers, hyperplasias and immature lungs, and serves as a marker for the relative activation of the hedgehog pathway. In addition, tissues such as immature lung, that have high gli gene expression, are strongly affected by hedgehog inhibitors. Accordingly, it is contemplated that the detection of gli gene expression may be used as a powerful predictive tool to identity tissues 5 and disorders that will particularly benefit from treatment with a hedgehog antagonist.

Gli-1 expression levels are detected, either by direct detection of the transcript or by detection of protein levels or activity. Transcripts may be detected using any of a wide range of techniques that depend primarily on hybridization or probes to the gli-1 transcripts or to cDNAs synthesized therefrom. Well known techniques include Northern blotting, reverse-transcriptase PCR and microarray analysis of transcript levels. Methods for detecting Gli protein levels include Western blotting, immunoprecipitation, two-dimensional polyacrylamide gel electrophoresis (2D SDS-PAGE—preferably compared against a standard wherein the position of the Gli proteins has been determined), and mass spectroscopy. Mass spectroscopy may be coupled with a series of purification steps to allow high-throughput indentification of many different protein levels in a particular sample. Mass spectroscopy and 2D SDS-PAGE can also be used to identify post-transcriptional modifications to proteins including proteolytic events, ubiquitination, phosphorylation, lipid modification, etc. Gli activity may also be assessed by analyzing binding to substrate DNA or in vitro transcriptional activation of target promoters. Gel shift assay, DNA footprinting assays and DNA-protein crosslinking assays are all methods that may be used to assess the presence of a protein capable of binding to Gli binding sites on DNA. J. Mol. Med. 77(6):459-68 (1999); Cell 100(4): 423-34 (2000); Development 127 (19): 4923-4301 (2000).

In certain embodiments, gli transcript levels are measured and diseased or disordered tissues showing abnormally high gli levels are treated with a hedgehog antagonist. In other embodiments, the condition being treated is known to have a significant correlation with aberrant activation of the hedgehog pathway, even though a measurement of gli expression levels is not made in the tissue being treated. Premature lung tissue, lung cancers (e.g., adeno carcinomas, bronco-alveolar adenocarcinoma, small cell carcinomas), breast cancers (e.g., inferior ductal carcinomas, inferior lobular carcinomas, tubular carcinomas), prostate cancers (e.g., adenocarcinomas), and benign prostatic hyperplasias all show strongly elevated gli-1 expression levels in certain cases. Accordingly, gli-1 expression levels are a powerful diagnostic device to determine which of these tissues should be treated with a hedgehog antagonist. In addition, there is substantial correlative evidence that cancers of the urothelial cells (e.g., bladder cancer, other urogenital cancers) will also have elevated gli-1 levels in certain cases. For example, it is known that loss of heterozygosity on chromosome 9q22 is common in bladder cancers. The ptch-1 gene is located at this position and ptch-1 loss of function is probably a partial cause of hyperproliferation, as in many other cancer types. Accordingly, such cancers would also show high gli expression and would be particularly amenable to treatment with a hedgehog antagonist.

Expression of ptch-1 and ptch-2 is also activated by the hedgehog signaling pathway, but not typically to the same extent as gli genes, and as a result are inferior to the gli genes as markers of hedgehog pathway activation. In certain tissues, only one of ptch-1 or ptch-2 is expressed although the hedgehog pathway is highly active. For example, in testicular development, desert hedgehog plays an important role and the hedgehog pathway is activated, but only ptc-2 is expressed. Accordingly, these genes may be individually unreliable as markers for hedgehog pathway activation, although simultaneous measurement of both genes is contemplated as a more useful indicator for tissues to be treated with a hedgehog antagonist.

Because gli is so ubiquitously expressed during hedgehog activation, any degree of gli overexpression can also be useful in combination with detection of hedgehog itself in determining that a hedgehog antagonist will be an effective therapeutic. In such embodiments, gli can be expressed at a level at least twice as high as normal. In particular embodiments, expression is four, six, eight or ten times as high as normal.

In light of the broad involvement of hedgehog signaling in the formation of ordered spatial arrangements of differentiated tissues in vertebrates, the hedgehog antagonists could be used in a process for generating and/or maintaining an array of different vertebrate tissue both in vitro and in vivo. The anti-hedgehog antibodies can be used to identify when the application of a hedgehog antagonist, whether inductive or anti-inductive with respect to proliferation or differentiation of a given tissue type, can be, as appropriate, any of the preparations described above.

C. Neuronal Cell Culture

The hedgehog antibodies are further applicable to identify cell culture techniques wherein reduction in hedgehog signaling, and hence application of hedgehog antagonists is desirable. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). Once use of the present method may be in culture of neuronal stem cells, such as in the use of such cultures for the generation of new neurons and glia. These cultures can be contacted with hedgehog antagonists in order to alter the rate of proliferation or neuronal stem cells in the culture and/or alter the rate of differentiation, or to maintain the integrity of a culture of certain terminally differentiated neuronal cells. In an exemplary embodiment, the subject method can be used to culture, certain neuron types (e.g., sensory neurons, motor neurons). Such neuronal cultures can be used as convenient assay systems as well as sources of implantable cells for therapeutic treatments.

The anti-hedgehog antibodies of the present invention may be applicable to a method of intracerebral grafting, an emerging treatment for disorders of the central nervous system. For example, one approach to repairing damaged brain tissues involves the transplantation of cells from fetal or neonatal animals into the adult brain. Dunnett et al., J. Exp. Biol. 123: 265-289 (1987). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The subject method can be used to monitor the regulation by hedgehog and/or hedgehog antagonists of the growth state in a culture, or where fetal tissue is used, especially neuronal stem cells, can be used to monitor the rate of differentiation of the stem cells induced by hedgehog and/or hedgehog antagonists.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The anti-hedgehog antibodies of the present invention can monitor the effectiveness of the hedgehog antagonists applied to cultured stem cells, so as to monitor the regulation of differentiation of the uncommitted progenitor, or to monitor the regulation of the developmental fate of a committed progenitor, or to monitor the regulation of the developmental fate of a committed progenitor cell towards becoming a terminally differentiated neuronal cell. For example, the present method can be used in vitro to monitor the regulation of the differentiation of neural crest cells into glial cells, schwann cells, chromaffin cells, cholinergic, sympathetic or parasympathetic neurons, as well as peptidergic and serotonergic neurons. The hedgehog antagonist can be used alone, or in combination with other neurotrophic factors that act to more particularly enhance a particular differentiation fate of the neuronal progenitor cell.

D. Regulation of Neuronal Growth and Differentiation

In addition to using the anti-hedgehog antibodies of the present invention in combination with hedgehog antagonists in the context of implantation of cell cultures, another aspect of the present invention relates to monitoring the therapeutic application of hedgehog antagonists to regulate the growth state of neurons and other neuronal cells in both the central nervous system and the peripheral nervous system. The ability of the hedgehog pathway component (e.g., ptch, hedgehog, and smoothened) to regulate neuronal differentiation during development of the nervous system and also presumably in the adult state indicates that in certain instances, the subject hedgehog antagonists can be expected to facilitate control of adult neurons with regard to maintenance, functional performance, and aging of normal cells; repair and regeneration processes in chemically or mechanically lesioned cells; and treatment of degeneration in certain pathological conditions. In light of this understanding, the present invention specifically contemplated applications of the subject method to the treatment (e.g., prevention, reduction in severity, etc.) of neurological conditions deriving from: (i) acute, subacute, or chronic injury to the nervous system, including traumatic injury, chemical injury, vascular injury and deficits (such as the isehemia resulting from stroke), together with infectious/inflammatory and tumor-induced injury; (ii) aging of the nervous system, including Parkinson's disease, Huntington's chorea, amyotrophic lateral sclerosis and the like, as well as spinocerebellar degeneration; and (iv) chronic immunological diseases of the nervous system or affecting the nervous system, including multiple sclerosis.

As appropriate, the subject method can also be used in generating nerve prosthesis for the repair of central and peripheral nerve damage. In particular, where a crushed or severed axon is intubulated by the use of a prosthetic device, hedgehog antagonists can be added to the prosthetic device to regulate the rate of growth and regeneration of the dendritic processes. Exemplary nerve guidance channels are described in U.S. Pat. Nos. 5,092,871 and 4,955,892.

In another embodiment, the subject method can be used in the treatment of neoplastic or hyperplastic transformation such as may occur in the central nervous system. For instance, the hedgehog antagonists can be utilitized to cause such transformed cells to become either post-mitotic or apoptotic. The present method may, therefore, be used as part of a treatment for, e.g., malignant gliomas, meningiomas, medulloblastomas, neuroectodermal tumors, and ependymomas.

E. Neuronal Cancer

The anti-hedgehog antibodies of the present invention can be used in combination with hedgehog antagonists may be used as part of a treatment regimen for malignant medulloblastoma and other primary CNS malignant neuroectodermal tumors. Medulloblastoma, a primary brain tumor, is the most common brain tumor in children. A medulloblastoma is a primitive neuroectodermal (PNET) tumor arising in the posterior fossa. They account for approximately 25% of all pediatric brain tumors. Histologically, they are small round cell tumors commonly arranged in true rosette, but may display some differentiation to astrocytes, ependymal cells or neurons. PNETs may arise in other areas of the brain including the penial gland (pineoblastoma) and cerebrum. Those arising in the supratentorial region generally have a worsened prognosis.

Medulloblastoma/PNETs are known to recur anywhere in the CNS after resection, and can even metastasize to bone. Pretreatment evaluation should therefore include and examination of the spinal cord to exclude the possibility of "dropped metastases". Gadolinium-enhanced MRI has largely replaced myelography for this purpose, and CSF cytology is obtained postoperatively as a routine procedure. The anti-hedgehog antibodies of the invention can used to detect hedgehog expression levels in either primary, and/or metastatic tumors, as part of treatment regimen to determine the effectiveness of a hedgehog antagonist.

In other embodiment, the subject method is used as part of a treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. In the CHOP series of 51 children reported with ependymomas, ¾ were histologically benign. Approximately ⅔ arose from the region of the $4^{th}$ ventricule. One third presented in the supratentorial region. Age at presentation peaks between birth and 4 years, as demonstrated by SEER data as well as data from CHOP.

The median age is about 5 years. Because so many children with this disease are babies, they often require multimodal therapy.

F. Non-Neuronal Cell Culture

The anti-hedgehog antibodies can be used in combination with hedgehog antagonists in cell culture and therapeutic methods relating to the generation and maintenance of non-neuronal tissue. Such uses are contemplated as a result of the involvement of hedgehog signaling components (e.g., ptch, hedgehog, smo, etc.) in morphogenic signals of other vertebrate organogenic pathways, such as endodermal patterning, and mesodermal and endodermal differentiation.

Hedgehog signaling, especially ptc, hedgehog, and smoothened, are involved in controlling the development of stem cells responsible for formation of the digestive tract, liver, lungs, and other organs derived from the primitive gut. Shh is the inductive signal from the endoderm to the mesoderm, which is critical to gut morphogenesis. Therefore, for example, the anti-hedgehog antibodies of the instant method can be employed in combination with hedgehog antagonists for regulating the development and maintenance of an artificial liver that can have multiple metabolic functions of a normal liver. In an exemplary embodiment, the subject method can be used to monitor the regulation by hedgehog antagonist of the functions of a normal liver. For example, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, the subject method can be employed therapeutically to monitor the regulation of such organs by hedgehog antagonist after physical, chemical or pathological insult. For instance, therapeutic comprising hedgehog antagonists can be used in liver repair subsequent to a partial hepactectomy.

In another embodiment, the subject method can be used to monitor the proliferation and/or differentiation of pancreatic tissue by hedgehog antagonists both in vivo and in vitro. The generation of the pancreas and small intestine from the embryonic gut depends on intercellular signaling between the endodermal and mesodermal cells of the gut. In particular, the differentiation of intestinal mesoderm into smooth muscle has been suggested to depend on signals from adjacent endodermal cells. One candidate mediator of endodermally derived signals in the embryonic hin dgut is Sonic hedgehog (Shh). Apelqvist et al., Curr. Biol. 7: 801-4 (1997). The Shh gene is expressed throughout the embryonic bud endoderm with the exception of the pancreatic bud endoderm, which instead expressed high levels of the homeodomain protein Ipf1/Pdx1 (insulin promoter factor 1/pancreatic and duodenal homeobox 1), an essential regulator of early pancreatic development. The Ipf1/Pdx1 was used to selectively express Shh in the developing pancreatic epithelium. The pancreatic mesoderm of Ipf1/Pdx1-Shh transgenic mice developed into smooth muscle and insterstitial cells of Cajal—cells which are characteristic of the intestine, rather than pancreatic mesenchyme and spleen. Apelqvist et al., supra. Also, pancreatic explants exposed to Shh underwent as similar expression of endodermally derived Shh controls the fate of adjacent mesoderm at different regions of the gut tube.

In another embodiment, the anti-hedgehog antibodies hedgehog antagonists are used to monitor the generation of endodermal tissue from non-endodermal stem cells including mesenchymal cells and stem cells derived from mesodermal tissues resulting from application of hedgehog antagonist. Exemplary mesodermal tissues from which stem cells may be isolated include skeletal muscle, cardiac muscle, kidney, cartilage and fat.

G. Pancreatic Conditions/Disorders

There are a wide variety of pathological cell proliferative and differentiative pancreatic conditions for which the anti-hedgehog antibodies of the present invention when used in combination with hedgehog antagonists may provide therapeutic benefits. More specifically, such therapeutic benefits are directed to correcting aberrant insulin expression, or modulation of differentiation of pancreatic cells. More generally, however, the present invention relates to a method of inducing and/or maintaining a differentiated state, enhancing survival and/or affecting proliferation of pancreatic cells, by contacting the cells with the subject hedgehog antagonists. For instance, in light of the apparent involvement of ptc, hedgehog and smoothened in the formation of ordered spatial arrangements of pancreatic tissues, the subject method could be used as part of a technique to monitor the generation and/or maintenance of such tissue both in vitro and in vivo. For instance, monitoring the modulation of hedgehog signaling can be employed in both cell culture and therapeutic methods involving generation and maintenance of β-islet cells and possibly also from nonpancreatic tissue, such as in controlling the development and maintenance of tissue from the digestive tract, spleen, lungs, urogenital organs (e.g., bladder), as well as other organs which derive from the primitive gut.

In a specific embodiment, the anti-hedgehog antibodies of the present invention, when used in combination with hedgehog antagonists can be used in the treatment of hyperplastic and neoplastic disorders affecting pancreatic tissue, especially those characterized by aberrant proliferation of pancreatic cells. For instance, pancreatic cancers are marked by abnormal proliferation of pancreatic cells, which can result in alterations of insulin secretory capacity of the pancreas. For instance, certain pancreatic hyperplasias, such as pancreatic carcinomas, can result in hypoinsulinemia due to dysfunction of β-cells or decreased islet cell mass. Moreover, manipulation of hedgehog signaling properties at different points may be useful as part of a strategy for reshaping/repairing pancreatic tissue both in vivo and in vitro. In one embodiment, the present invention makes use of the apparent involvement of ptc, hedgehog and smoothened in regulating the development of pancreatic tissue. In another embodiment, the subject anti-hedgehog antibodies, when used in combination with hedgehog antagonists, can be employed therapeutically to regulate the pancreas after physical, chemical or pathological insult. In yet another embodiment, the subject method can be applied to cell culture techniques, and in particular, may be employed to enhance the initial integration of prosthetic pancreatic tissue devices. Manipulation of proliferation and differentiation of pancreatic tissue, such as through using hedgehog antagonists, can provide a means for more carefully controlling the characteristics of a cultured tissue. In an exemplary embodiment, the subject method can be used to augment production of prosthetic devise which require β-islet cells, such as may be used in the encapsulation devices described in, for example, as described in U.S. Pat. Nos. 4,892,538, 5,106,627, 4,391,909 and 4,353,888. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embryonal traits in mature β-cells can be observed. By utilizing the subject anti-hedgehog antibodies, antagonists, one can monitor the differentiation path or proliferative index of the cells regulated by hedgehog antagonists.

Furthermore, monitoring the manipulation by hedgehog antagonists of the differentiative state of pancreatic tissue can be utilized in conjunction with transplantation of artificial pancreas. For instance, manipulation of hedgehog function to affect tissue differentiation can be utilized as a means of maintaining graft viability.

H. Cell Proliferative Disorders, Tumors and Cancers

The anti-hedgehog antibodies the present invention may also be used to combination with hedgehog antagonists to treat lung carcinoma and adenocarcinoma, and other proliferative disorders involving the lung epithelia. It is known that Shh is expressed in human lung squamous carcinoma and adenocarcinoma cells. Fujita et al., Biochem. Biophys. Res. Commun. 238: 658 (1997). The expression of Shh was also detected in the human lung squamous carcinoma tissues, but not in the normal lung tissue of the same patient. It was also observed that Shh stimulates the incorporation of BrdU into the carcinoma cells and stimulates their cell growth, while anti-Shh-H inhibited such growth. These results suggest that a ptc, hedgehog, and/or smoothened is involved in cell growth of such transformed lung tissue and therefore indicates that detecting the presence of hedgehog in such tissue may be determinative to identify whether hedgehog antagonists can be used to treat such lung carcinoma and adenocarcinomas, and other such proliferative disorders involving the lung epithelia.

The anti-hedgehog antibodies hedgehog antagonists of the present invention may also be used to identify tumors in which the existence or pathogenesis is associated with hedgehog signaling, and thus would be responsive to the application of hedgehog antagonists. Such tumors include, but are not limited to: tumors related to Gorlin's syndrome (e.g., medulloblastoma, meningioma, etc.), tumors evidence in ptc knock-out mice (e.g., hemangioma, rhabdomyosarcoma, etc.), tumors resulting from gli-1 amplification (e.g., glioblastoma, sarcoma, etc.), tumors resulting from Smo dysfunction (e.g., basal cell carcinoma, etc.), tumors connected with TRC8, a ptc homolog (e.g., renal carcinoma, thyroid carcinoma, etc.), Ext-1 related tumors (e.g., bone cancer, etc.), Shh-induced tumors (e.g., lung cancer, chondrosarcomas, etc.), and other tumors (e.g., breast cancer, urogenital cancer (e.g., kidney, bladder, ureter, prostate, etc.), adrenal cancer, gastrointestinal cancer (e.g., stomach, intestine, etc.).

The anti-hedgehog antibodies of the present invention may also to identify cancer that would be responsive to the application of hedgehog antagonists. These cancer include, but are not limited to: prostate cancer, bladder cancer, biliary cancer, lung cancer (including small cell and non-small cell), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional cancer types include cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer. Further exemplary forms of cancer which can be treated with the hedgehog antagonists of the present invention include cancers comprising hedgehog expressing cells. Still further exemplary forms of cancer which can be treated with the hedgehog antagonists of the present invention include cancers comprising gli expressing cells. In one embodiment, the cancer is not characterized by a mutation in patched-1.

K. Epithelial Tissue

The anti-hedgehog antibodies of the invention also may be used to identify epithelial tissue that would be susceptible for the therapeutic treatment (including prophylaxis) of disorders by hedgehog antagonists. In general, such a treatment comprises administering an amount of a hedgehog antagonist effective to alter the growth state of the treated epithelial tissue that is responsive to hedgehog signaling. The mode of administration and dosage regimens will vary depending on the epithelial tissue(s) that is to be treated (e.g., dermal, mucosal, glandular, etc.). In a specific aspect, the method can be used to regulate the induction of Shh induced differentiation and/or inhibit proliferation of epithelially derived tissue. Thus, the anti-hedgehog antibodies of the present invention can be used in a method for the treatment of hyperplastic and/or neoplastic conditions involving epithelial tissue that is responsive to hedgehog antagonists.

(1) Hair Growth

The anti-hedgehog antibodies of the invention can also be used in combination with hedgehog antagonists control hair growth. Hair is basically composed of keratin, a tough and insoluble protein. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, method for increasing or reducing hair growth can be carried out by potentiating or inhibiting, respectively, the proliferation of these stem cells.

The anti-hedgehog antibodies can be used to identify tissues that would be responsive to the application of hedgehog antagonists in a method of reducing the growth of human hair, either as a replacement to or in combination with removal by cutting, shaving, or depilation. For instance, the present method can be used in the treatment of trichosis characterized by abnormally rapid or severe growth of hair, e.g., hypertrichosis. In an exemplary embodiment, hedgehog antagonists can be used to manage hirsutism, a disorder marked by abnormal hairiness. The subject method can also provide a process for extending the duration of depilation.

Moreover, because a hedgehog antagonist will often be cytostatic to epithelial cells, rather than cytotoxic, such agents can be used to protect hair follicle cells from cytotoxic agents that require cell progression into S-phase of the cell-cycle for efficacy, e.g., radiation-induced death. Treatment by the hedgehog antagonists can provide protection by causing the hair follicle cells to become quiescent, e.g., by preventing the cells from entering S-phase, and thereby preventing the follicle cells from undergoing mitotic catastrophe or programmed cells death. For example, the hedgehog antagonists can be used in patients undergoing chemo- or radiation-therapies that ordinarily result in hair loss. By inhibiting cellcycle progression during such therapies, the subject treatment can protect hair follicle cells from death, which might otherwise result from activation of cell death programs in the absence of quiescense. After therapy of the hedgehog antagonists has concluded, the instant method can also be removed with concomitant relief of the inhibition of follicle cell proliferation. The anti-hedgehog antibodies of the invention can be used to identify such tissue in which hedgehog signaling is active, and hence would benefit from the application of hedgehog antagonists.

The anti-hedgehog antibodies of the present invention can also be used to identify patients suffering from folliculitis, such as folliculitis decalvans, folliculitis ulerythematosis reticulate or keloid folliculitis that would be responsive to hedgehog antagonists. For example, a cosmetic preparation of a hedgehog antagonist can be applied topically in the treatment of pseudofolliculitis, a chronic disorder occurring most often in the submandibular region of the neck and associated with shaving, the characteristic lesions of which are erythematous papules and pustules containing buried hairs.

The hedgehog antagonists of the invention can be used to identify tissues that would be responsive to hedgehog antagonists in a method of modulating the growth of human hair. Sato et al., J. Clin. Invest. 104: 855-864 (1999) reported that upregulation of Shh activity in postnatal skin functions as a biologic switch that induces resting hair follicles to enter anagen with consequent hair growth. Sato et al., used an adenovirus vector, AdShh, to transfer the murine Shh cDNA to skin of postnatal day 19 C57BL/6 mice. The treated skin showed increased mRNA expression of Shh, Patched, and Gli-1. In mice receiving AdShh, but not in controls, acceleration into anagen was evident, since hair follicle size and melanogenesis increased and the hair-specific keratin ghHb-1 and the melanin synthesis-related tyrosinase mRNAs accumulated. Finally, C57BL/6 mice showed marked acceleration of the onset of new hair growth in the region of AdShh administration to skin weeks after treatment, but not in control vector-treated or untreated areas. After 6 months, AdShh-treated skin showed normal hair and normal skin morphology. Thus, the anti-hedgehog antibodies the present invention may be useful to identify when application of hedgehog antagonists would be useful to regulate or modulate Shh-induced hair growth.

(2) Excessive Epithelial Proliferation

The anti-hedgehog antibodies of the present invention can be used to identify hyperplastic conditions (e.g., keratosis) and neoplastic epidermal conditions characterized by a high proliferation rate (e.g., squamous cell carcinoma) that would be responsive to hedgehog antagonists. This includes the treatment of autoimmune diseases affecting the skin, in particular, or dermatological diseases involving morbid proliferation and/or keratinization of the epidermis, as for example, caused by psoriasis or atopic dermatosis. These anti-hedgehog antibodies could also be used to identify common skin disorders that are characterized by localized abnormal proliferation of the skin (e.g., psoriasis, squamous cell carcinoma, keratocanthoma, actinic keratosis) which would be expected to be treatable by application of the hedgehog antagonists.

The anti-hedgehog antibodies of the invention can also be used to identify variety of other disorders characterized by keratotic lesions that would be suitable for treatment with hedgehog antagonists. Actinic keratoses, for example, are superficial inflammatory premalignant tumors arising on sun-exposed and irradiated skin. Accordingly, treatment of keratosis, such as actinic keratosis, includes application of a hedgehog antagonist composition in amounts sufficient to inhibit hyperproliferation of epidermal/epidermoid cells of the lesion.

(3) Acne

Acne represents yet another dermatologic ailment which may be treated by the hedgheg antagonists. Acne vulgaris, a multifactor disease most commonly occurring in teenagers and young adults, is characterized by the appearance of inflammatory and noninflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by *Propinobacterium acnes* and *Staphylococcus epidermidis* bacteria and *Pitrosporum ovale*, a yeast. The anti-hedgehog antibodies of the present invention may be used to identify patients or tissues in which treatment with hedgehog antagonists would be effective. In particular, topical preparations, may be useful for preventing the transitional features of the ducts, e.g., hypercornification, which lead to lesion formation. Such a therapeutic regimen comprising hedgehog antagonists may further include in additional components, such as for example, antibiotics, retinoids and antiandrogens.

(4) Dermatitis and Other Skin Ailments

The anti-hedgehog antibodies of the present invention may also be used to identify patients or tissues suffering from dermatitis that would be responsive to hedgehog antagonists. Dermatitis is a descriptive term referring to poorly demarcated lesions that are either pruritic, erythematous, scaly, blistered, weeping, fissured or crusted. These lesions arise from any of a wide variety of causes. The most common types of dermatitis are atopic, contact and diaper dermatitis. For example, seborrheic dermatitis is a chronic, usually pruritic, dermatitis with erythema, dry, moist, or greasy scaling, and yellow-crusted patches on various areas, especially the scalp, with exfoliation of an excessive amount of dry scales. Hedgehog antagonists may also be used in the treatment of stasis dermatitis, an often chronic, usually eczematous dermatitis. Actinici dermatitis is a dermatitis that due to exposure to actinic radiation such as that from the sun, ultraviolet waves, or x- or gamma-radiation. According to the present invention, the subject method can be used in the treatment and/or prevention of certain symptoms of dermatitis caused by unwanted proliferation of epithelial cells. Such therapies for these various forms of dermatitis can also include topical and systemic corticosteroids, antipruritics, and antibiotics.

Additional ailments that may be treated by the subject method are disorders specific to non-humans, such as mange.

L. Non-Canonical Hedgehog Signaling

The anti-hedgehog antibodies of the present invention can be used to identify situations or conditions in which hedgehog antagonists can be used to regulate the activity in a noncanonical Shh pathway that is independent of the Patched-Smoothened receptor complex and the Gli transcription factors. In a recent report, Jarov et al., Dev. Biol. 261(2): 520-536 (2003), describes that, when Shh was immobilized to the substrate (extracellular matrix) or produced by neuroepithelial cells themselves after transfection, neural plate explants failed to disperse and instead formed compact structures. Changes in the adhesive capacities of neuroepithelial cells caused by Shh could be accounted for by inactivation of surface β1-integrins combined with an increase in N-cadherin-mediated cell adhesion. This immobilized-Shh-mediated adhesion does not contradict or interfere with the previously known (soluble) Shh-mediated inductive, mitogenic, and trophic functions, since the immobilized Shh promoted differentiation of neuroepithelial cells into motor neurons and floor plate cells with the same potency as soluble Shh. It has also been demonstrated that Shh-regulation of adhesion properties during neural tube morphogenesis is rapid and reversible, and it does not involve the classical Patched-Smoothened-Gli signaling pathway, and it is independent and discernible from Shh-mediated cell differentiation. Thus, modifications of the adhesive properties of neural epithelial cells induced by Shh cannot be attributed to its differentiation promoting effect, but reveal a novel function of Shh in this tissue that has not been described previously. Thus, the anti-hedgehog antibodies of the present invention can identify conditions where hedgehog antagonists of the present invention may be used to regulate this non-canonical hedgehog pathway that is independent of Ptch, Smo, Fu, Su(Fu) and/or Gli. More specifically, such hedgehog antagonists may be used in a method to disrupt this function in neuronal or other applicable tissues, preferably at specific developmental stages.

III. Compositions and Methods

A. Anti-Hedgehog Antibodies

Exemplary antibodies that may be used for such purposes include polyclonal and monoclonal antibodies. The term "antibodies" sometimes also include antigen-binding fragments.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, SOCl, or $R1N=C=NR$, where R and R1 are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells. Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

3. Antibody Fragments

In certain circumstances there are advantages of using antibody fragments, rather than whole antibodies.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and scFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869, 046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641, 870 for example. Such linear antibody fragments may be monospecific or bispecific.

B. Variants of Anti-Hedgehog Antibodies

In addition to the anti-hedgehog antibodies described herein, it is contemplated that variants of such molecules can be prepared for use with the invention herein. Such variants can be prepared by introducing appropriate nucleotide changes into the encoding DNA, and/or by synthesis of the desired antibody or polypeptide. Those skilled in the art will appreciate that amino acid changes may alter posttranslational processes of these molecules, such as changing the number or position of glycosylation sites so as to enhance the hedgehog binding properties. Variations in amino acid sequence can be made, for example, using any of the techniques and guidelines for conservative and non-conservative mutations set forth, for instance, in U.S. Pat. No. 5,364,934. Variations may be a substitution, deletion or insertion of one or more codons encoding the amino acid sequence that results in a change in the amino acid sequence as compared with the native sequence. Optionally the variation is by substitution of at least one amino acid with any other amino acid in one or more of the domains of the amino acid sequence of interest. Guidance in determining which amino acid residue may be inserted, substituted or deleted without adversely affecting the desired activity may be found by comparing the sequence of the amino acid sequence of interest with homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Fragments of the various anti-hedgehog antibodies are provided herein. Such fragments may be truncated at the N-terminus or C-terminus, or may lack internal residues, for example, when compared with a full length native antibody or protein. Such fragments which lack amino acid residues that are not essential for a desired biological activity are also useful with the disclosed methods.

The above polypeptide fragments may be prepared by any of a number of conventional techniques. Desired peptide fragments may be chemically synthesized. An alternative approach involves generating such fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding the desired fragment by polymerase chain reaction (PCR). Oligonucleotides that define the desired termini of the DNA fragment are employed at the 5' and 3' primers in the PCR. Preferably, such fragments share at least one biological and/or immunological activity with the corresponding full length molecule.

In particular embodiments, conservative substitutions of interest are shown in 5 Table 1 under the heading of preferred substitutions. If such substitutions result in a change in biological activity, then more substantial changes, denominated exemplary substitutions in Table 1, or as further described below in reference to amino acid classes, are introduced and the products screened in order to identify the desired variant.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Pro; Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Leu |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the anti-hedgehog antibody variants are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: Norleucine, Met, Ala, Val, Leu, Ile;
(2) neutral hydrophilic: Cys, Ser, Thr; Asn; Gln
(3) acidic: Asp, Glu;
(4) basic: His, Lys, Arg;
(5) residues that influence chain orientation: Gly, Pro; and
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the anti-hedgehog antibody molecule.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science, 244:1081-1085 (1989)]. Alanine is also typically preferred because it is the most common amino acid. Further, it is frequently found in both buried and exposed positions [Creighton, The Proteins, (W.H. Freeman & Co., N.Y.); Chothia, J. Mol. Biol., 150:1 (1976)]. If alanine substitution does not yield adequate amounts of variant, an isoteric amino acid can be used.

Any cysteine residue not involved in maintaining the proper conformation of the anti-hedgehog antibody variant also may be substituted, generally with serine, to improve the oxidative stability of the molecule and prevent aberrant crosslinking. Conversely, cysteine bond(s) may be added to such a molecule to improve its stability (particularly where the antibody is an antibody fragment such as an Fv fragment).

A particularly preferred type of substitutional variant involves substituting one or more residues of a binding region of the antibody. For example, in the case of an anti-hedgehog antibody, a hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and target polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of anti-hedgehog antibody variants are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of a native sequence or an earlier prepared variant.

C. Preparation of Anti-Hedgehog Antibodies

The description below relates primarily to production of anti-hedgehog antibodies by culturing cells transformed or transfected with a vector containing nucleic acid encoding such antibodies. It is, of course, contemplated that alternative methods, which are well known in the art, may be employed to prepare such antibodies. For instance, the appropriate amino acid sequence, or portions thereof, may be produced by direct peptide synthesis using solid-phase techniques [see, e.g., Stewart et al., Solid-Phase Peptide Synthesis, W.H. Freeman Co., San Francisco, Calif. (1969); Merrifield, J. Am. Chem. Soc., 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of such antibodies may be chemically synthesized separately and combined using chemical or enzymatic methods to produce the desired product.

1. Selection and Transformation of Host Cells

Host cells are transfected or transformed with expression or cloning vectors described herein for anti-hedgehog antibody production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: A Practical Approach, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with Agrobacterium tumefaciens is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456-457 (1978) can be employed. General aspects of mammalian cell host system transfections have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing 5 DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527-537 (1990) and Mansour et al., Nature, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kanr 25; *E. coli* W3110 strain 37D6, which has the complete genotype tonA ptr3 phoA E15 (argF-lac)169 degP ompT rbs7 ilvG kanr; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

Full length antibody and antibody fragments can be produced in bacteria, in particular when glycosylation and Fc effector function are not needed. Full length antibodies have greater half life in circulation. Production in *E. coli* can be faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed in suitable cells (e.g., CHO cells).

In addition to prokaryotes, eukaryotic microbes such as filamentous fungi or yeast are suitable cloning or expression hosts for vectors encoding hedgehog polypeptides. *Saccharomyces cerevisiae* is a commonly used lower eukaryotic host microorganism. Others include *Schizosaccharomyces pombe* (Beach and Nurse, Nature, 290: 140 [1981]; EP 139,383 published 2 May 1985); *Kluyveromyces* hosts (U.S. Pat. No. 4,943,529; Fleer et al., Bio/Technology, 9:968-975 (1991)) such as, e.g., *K. lactis* (MW98-8C, CBS683, CBS4574; Louvencourt et al., J. Bacteriol., 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., Bio/Technology, 8:135 (1990)), *K. thermotolerans*, and *K. marxianus*; *yarrowia* (EP 402,226); *Pichia pastoris* (EP 183,070; Sreekrishna et al., J. Basic Microbiol., 28:265-278 [1988]); *Candida*; *Trichoderma reesia* (EP 244,234); *Neurospora crassa* (Case et al., Proc. Natl. Acad. Sci. USA, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., Biochem. Biophys. Res. Commun., 112:284-289 [1983]; Tilburn et al., Gene, 26:205-221 [1983]; Yelton et al., Proc. Natl. Acad. Sci. USA, 81: 1470-1474 [1984]) and *A. niger* (Kelly and Hynes, EMBO J., 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, The Biochemistry of Methylotrophs, 269 (1982).

Suitable host cells for the expression of glycosylated hedgehog kinase polypeptide production are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 5 cells; and a human hepatoma line (Hep G2).

Host cells are transformed with the above-described expression or cloning vectors for antihedgehog antibody production and cultured in conventional nutrient media modified as appropriate for inducing promoters, selecting transformants, or amplifying the genes encoding the desired sequences.

2. Selection and Use of a Replicable Vector

The nucleic acid (e.g., cDNA or genomic DNA) encoding the respective anti-hedgehog antibody may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The light and heavy chains of the anti-hedgehog antibody may be expressed not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the DNA encoding the mature sequence that is inserted into the vector. The signal sequence may be a prokaryotic signal sequence selected, for example, from the group of the alkaline phosphatase, penicillinase, 1 pp, or heatstable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up nucleic acid encoding the desire protein, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trp1 gene present in the yeast plasmid YRp7 [Stinchcomb et al., Nature, 282:39 (1979); Kingsman et al., Gene, 7:141 (1979); Tschemper et al., Gene, 10:157 (1980)]. The trp1 gene provides a selection marker for a mutant strain of yeast lacking the ability to grow in tryptophan, for example, ATCC No. 44076 or PEP4-1 [Jones, Genetics, 85:12 (1977)].

Expression and cloning vectors usually contain a promoter operably linked to the nucleic acid sequence encoding the desired amino acid sequence, in order to direct mRNA synthesis. Promoters recognized by a variety of potential host cells are well known. Promoters suitable for use with prokaryotic hosts include the β-lactamase and lactose promoter systems [Chang et al., Nature, 275:615 (1978); Goeddel et al., Nature, 281:544 (1979)], alkaline phosphatase, a tryptophan (tip) promoter system [Goeddel, Nucleic Acids Res., 8:4057 (1980); EP 36,776], and hybrid promoters such as the tac promoter [deBoer et al., Proc. Natl. Acad. Sci. USA, 80:21-25 (1983)]. Promoters for use in bacterial systems also will contain a Shine-Dalgarno (S.D.) sequence operably linked to the DNA encoding the desired protein sequence.

Examples of suitable promoting sequences for use with yeast hosts include the promoters for 3-phosphoglycerate kinase [Hitzeman et al., J. Biol. Chem., 255:2073 (1980)] or other glycolytic enzymes [Hess et al., J. Adv. Enzyme Reg., 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

DNA Transcription in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the anti-hedghog antibody may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the coding sequence of the preceding amino acid sequences, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the respective antibody, polypeptide or oligopeptide described in this section.

Still other methods, vectors, and host cells suitable for adaptation to the synthesis of the respective antibody, polypeptide or oligopeptide in recombinant vertebrate cell culture are described in Gething et al., Nature, 293:620-625 (1981); Mantei et al., Nature, 281:40-46 (1979); EP 117,060; and EP 117,058.

3. Culturing the Host Cells

The host cells used to produce the anti-hedgehog antibodies may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

4. Detecting Gene Amplification/Expression

Gene amplification and/or expression may be measured in a sample directly, for example, by conventional Southern blotting, Northern blotting to quantitate the transcription of mRNA [Thomas, Proc. Natl. Acad. Sci. USA, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies suitable for the present method may be prepared against a native sequence polypeptide or against exogenous sequence fused to DNA and encoding a specific antibody epitope of such a polypeptide or oligopeptide.

5. Purification

Anti-Hedgehog antibodies may be recovered from culture medium or from host cell lysates. If membrane-bound, it can be released from the membrane using a suitable detergent solution (e.g. Triton-X 100) or by enzymatic cleavage. Cells employed in expression of the preceding can be disrupted by various physical or chemical means, such as freeze-thaw cycling, sonication, mechanical disruption, or cell lysing agents.

It may be desirable to purify the preceding from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex® G-75; protein A Sepharose® columns to remove contaminants such as IgG; and metal chelating columns to bind epitope-tagged forms of the desired molecules. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular antibody, polypeptide or oligopeptide produced for the claimed methods.

When using recombinant techniques, the anti-hedgehog antibodies can be produced intracellularly, in the periplasmic space, or directly secreted into the medium. If such molecules are produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon® or Millipore ultrafiltration unit. A protease inhibitor such as PMSF may be included in any of the foregoing steps to inhibit proteolysis and antibiotics may be included to prevent the growth of adventitious contaminants.

Purification can occur using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma 1$, $\gamma 2$ or $\gamma 4$ heavy chains (Lindmark et al., J. Immunol. Meth. 62:1-13 (1983)). Protein G is recommended for all mouse isotypes and for human $\gamma 3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H 3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin Sepharose® chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

D. Articles of Manufacture and Kits

For therapeutic applications, the article of manufacture comprises a container and a label or package insert on or associated with the container indicating a use for the detection of hedgehog expression, including in combination with a hedgehog antagonist. Suitable containers include, for example, bottles, vials, syringes, etc. The containers may be formed from a variety of materials such as glass or plastic. The container holds the composition comprising the anti-hedgehog antibody and may have a sterile access port. The label or package insert indicates that the composition is used for detecting hedgehog expression. The label or package insert will further comprise instructions for using the anti-hedgehog antibody.

Kits may also be provided that are useful for various other purposes, e.g., for hedgehog-expressing cell killing assays, for purification or immunoprecipitation of hedgehog from cells. For isolation and purification of hedgehog kinase polypeptide, the kit can contain the respective hedgehog kinase-binding reagent coupled to beads (e.g., Sepharose® beads). Kits can be provided which contain such molecules for detection and quantitation of hedgehog polypeptide in vitro, e.g., in an IHC, ICC, ISH, EIA, ELISA or a Western blot. As with the article of manufacture, the kit comprises a container and a label or package insert on or associated with the container. The container holds a composition comprising at least one such anti-hedgehog antibody molecule useable with the invention. Additional containers may be included that contain, e.g., diluents and buffers, control antibodies. The label or package insert may provide a description of the composition as well as instructions for the intended in vitro or diagnostic use.

EXAMPLES

Example 1

Preparation of anti-Hh antibodies

Antigen Preparation:

The N-terminus of human Shh (aa 24-197) was subcloned into the pST293 vector with an Nterminal unizyme histidine (HQ) tag in place of the native signal sequence under a phoA promoter and transformed into 58F3 *E. Coli*. A starter culture was diluted 1:100 in 500 ml C.R.A.P. phosphate limiting media with 50 µ/ml carbencillin for 24 h at 30° C. The phoA promoter induces protein expression once phosphate is depleted from the media at an $OD_{600}$ of ~2 (about 7 h later), at which time 100 µM zinc sulfate was added to help Shh folding. The cell pellet was resuspended in 5 volumes (w/v) of lysis buffer (25 mM sodium phosphate pH 8.0, 0.15 mM NaCl, 1 mM EDTA, 1 mM PMSF, 10 mM β-mercaptoethanol) with a Polytron PT300 and lysed by three passes through a microfluidizer at 10,000 psi. The homogenate was centrifuged at 14,000 g for 60 min at 4° C. and Mes pH 5.0 was added to 50 mM final concentration. The lysate was loaded onto a 5 ml HiTrap™ SPHP (Pharmacia) column previously equilibrated with buffer A (25 mM sodium phosphate pH 5.5, 10 mM β-mercaptoethanol) containing 150 mM NaCl. The column was washed with 4 column volumes (CV) of buffer A, followed by 4 CV of buffer A containing 150 mM NaCl, and protein was eluted with a 0.3-1.0 M NaCl gradient in the same buffer. Fractions containing Shh (based on SDS-PAGE analysis) were pooled, imidazole (pH 7.0) was added to a final concentration of 20 mM, and the material was loaded onto a 5 ml His Trap (Pharmacia) column equilibrated with buffer B (25 mM sodium phosphate pH 8.0, 300 mM NaCl, 10 mM s-mercaptoethanol). After washing with 5 CV of 20 mM imidazole in buffer B and 5 CV of a 20-50 mM imidazole gradient, the protein was eluted with 5 CV of 250 mM imidazole in the same buffer. Eluted fractions were analyzed by SDS-PAGE, and the elution pool concentration was determined by absorbance at 280 nm using an extinction coefficient of 1.17 $(g/1)^{-1}$ $cm^{-1}$ for Shh. The protein was sterilized by 0.2 µM filtration and single-use aliquots stored at –80° C., then thawed in cold water immediately prior to use.

Generation of anti-Shh rabbit polyclonal antibodies 250 µg of the his-Shh-N antigen prepared by the procedure described above was injected into each of two 3-month old New Zealand white rabbits (numbered 59A and 59B) using 1:1 antigen:complete Freund's Adjuvant, followed by boosting every other week (with a break between weeks 30 and 41) with 1:1 antigen:incomplete Freund's Adjuvant (Josman labs, LLC). Immune sera were titered by serial dilution ELISA on the same antigen (Antibody Solutions, Mountain View, Calif.), with rabbit 59A having a maximal titer of 1:200 000 at week 9 and rabbit 59B over 1: 2 000 000 at week 11. Bleeds from weeks 7-11 of rabbit 59A and weeks 3-11 of rabbit 59B were affinity purified on the Shh-N antigen bound to CNBr activated Sepharose® beads and the purified antibodies dialyzed against PBS and flash-frozen in aliquots for storage at –20° C. For comparison, the rabbit polyclonal anti-Shh antibody H-160 (Santa Cruz sc-902, lot#K0104) was raised against the human Shh aa fragment 41-200.

Generation of Anti-Shh Rabbit Monoclonal Antibodies

Following boosts at weeks 45 and 52, the spleen of rabbit 59B (with a titer of 1: 15 000 at week 46) was excised to rabbit myeloma cells (240-E1, Epitomics). The hybridoma supernatants were screened by ELISA on HQ-hShh-N antigen and the positive ones (32) further screened for reactivity on PFA-fixed hShh-transfected COS cells by immunofluorescence followed by formalin-fixed, paraffin-embedded hShh transfected 293 cells by immunohistochemistry as described below. The 4 chosen clones were expanded, subcloned by limiting dilution and re-tested as above. The three best subclones from the single remaining positive parent (#95) were selected for scale-up in Integra flasks 95.3, 95.7 and 95.9. After 3 months' growth in low-serum media the supernatants were purified on protein-A Sepharose®, yielding approximately 1 mg 95.3 (Shh:4667), 1.2 mg 95.7 (Shh:4668) and 2 mg 95.9 (Shh:4669).

Immunofluorescence

COS-7 cells were transiently transfected with untagged full-length human Shh (Accession NP_000184), Ihh (NP_002172) or Dhh (NP_066382) in pCMV.Sport6 using Lipofectamine™ 2000 (Invitrogen) reagent according to the manufacturer's protocol in 8-well LabTekII™ slides or 96-well black walled microscopy plates (Whatman) for screening. After 60 h transfection, cells were fixed with 3% PFA for 20 min at room temperature, quenched for 10 min in 50 mM ammonium chloride and permeabilized with 0.4% saponin (Sigma) in PBS containing 1% BSA and 2% FBS. Affinity purified rabbit polyclonals and monoclonals were used at 50 g/ml, while hybridoma supernatants were diluted 1:2. 5E1 monoclonal anti-Shh (Ericson/Jessell 1998 Cell 87 p661) at 10 g/ml was used as a positive control. Antibody staining was detected with Cy3-labeled donkey anti-rabbit (or mouse for 5E1) (Jackson Immunoresearch) and visualized by epifluorescence microscopy using a Discovery-1 high content screening microscope (Molecular Devices) and/or a DeltaVision (Applied Precision) microscope equipped with DAPI, FITC and rhodamine filters.

Immunohistochemistry

HEK293 cells were transiently transfected with untagged human Shh full length hShh (block H2006-223(5)), Dhh (H2006-1676) or hIhh (H2006-1677) in pcDNA3.1 using Lipofectamine™ 2000 (Invitrogen) reagent according to the manufacturer's protocol in ten 15 cm dishes and harvested 48 h later with 5 mM EDTA in PBS. Cell pellets were processed for formalin fixation and paraffin embedding according to standard protocols. In brief, the cells were fixed with 10% Neutral Buffered Formalin, processed in automated processors, paraffin-embedded (FFPE) and sectioned at 3 µm on Superfrost® Plus slides. Slides were then de-paraffinized and hydrated in water after treatment with a series of xylenes and alcohols in a Leica® autostainer and pre-treated for antigen retrieval with Dako® TARGET retrieval solution in PT module (Lab Vision); this method worked better than DakoR High pH and Triology retrieval methods for 95.9 antibodies. Endogenous peroxidase activity was then quenched by incubating the slides in KPL solution (KPL Laboratories) for 4 minutes at room temperature. After blocking endogenous immunoglobulins with blocking serum, slides were stained in a three-step protocol on a Dako® autostainer, employing various rabbit anti-Hh primary antibodies or neat hybridoma supernatants, followed by biotinylated anti rabbit secondaries (Vector Laboratories) then ABC complex (ABC Elite Kit-Vector Laboratories) and visualized using DAB (Pierce Laboratories) as a chromogen. To maximize detection of weak antibodies in supernatants, a further amplification step was added, using tyramide signal amplification (TSA) followed by Streptavidin-HRP (Perkin Elmer TSA kit) in place of ABC complex. Slides were then counterstained with Meyers Hematoxylin and dehydrated with series of alcohols and xylenes followed by coverslipping using organic mounting medium (Permamount). Naive rabbit IgG (Alpha Diagnostics) was used as negative control and rabbit anti-Hh H-160 (Santa Cruz Biotech Sc-9024) as a positive control. Staining with purified 95.9 rMab was optimal at 5 µg/ml, and both this and H-160 worked best without TSA amplification, to minimize background.

Hh Sandwich ELISA Assay.

ELISA plates were coated overnight at 4° C. with 5 µg/ml anti-Shh/Ihh monoclonal antibody AA.F10 (Curis, Inc) or 95.9 and incubated with increasing concentrations of recombinant octyl-Shh at room temperature for 1 h in assay diluent (0.5% BSA, 0.05% Tween20, 15 ppm proclin in PBS). After washing, bound octyl-Shh was detected by sequential incubations of 0.1 µg/ml biotinylated 5E1 anti-Hh (anti-Shh/Ihh/Dhh) for 1 h, 50 ng/ml streptavidin-HRP for 30 min, then visualized with TMB substrate and read at 650 nm. The ELISA was performed in triplicate and OD650 was plotted vs octyl-Shh concentration±standard deviation of the mean. Using AA.F10 as the coating Ab, this assay reproducibly detects octyl-Shh in the range of 78 pg/ml to 10 ng/ml.

Results

Generation of Rabbit Monoclonals to Hh.

Figure 2:
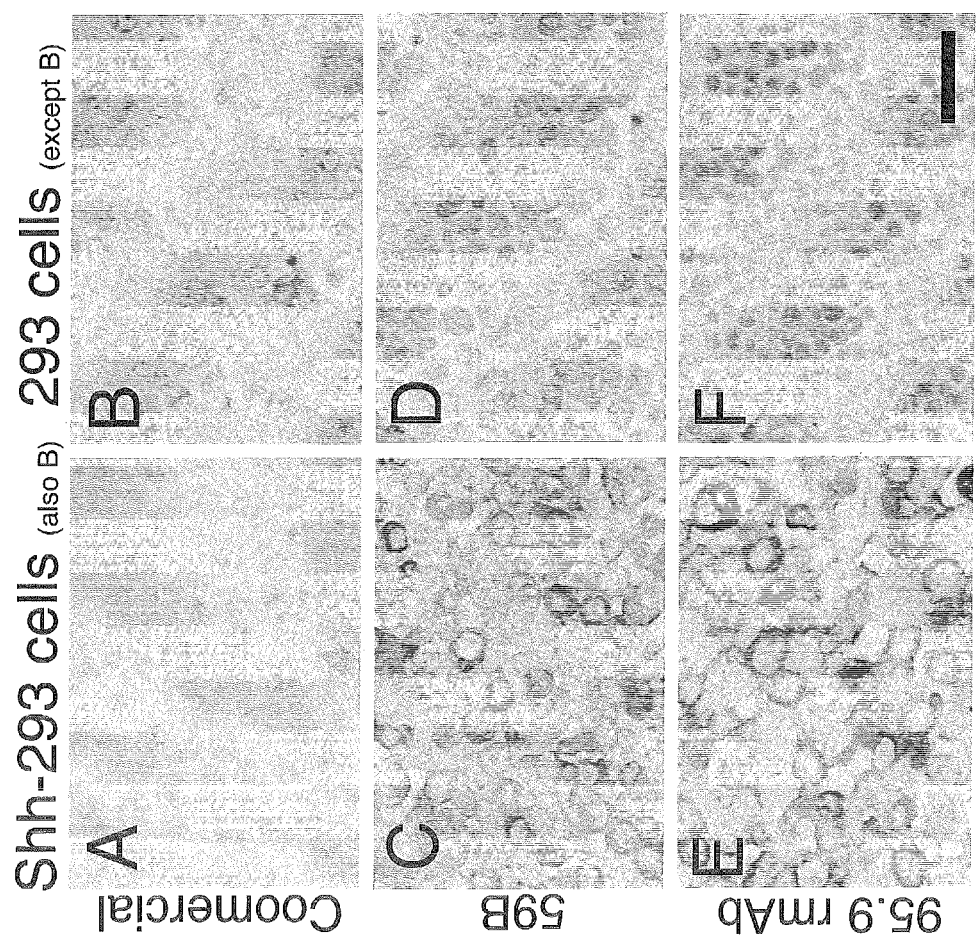
FIGS. 2A-F are micrographs demonstrating that polyclonal anti-Shh antibody ("59 pAb") and its derived rMAb specifically recognize Shh-transfected 293 cells by IHC. FFPE sections of untransfected (B, F) or human Shh transiently transfected (A, C, E) 293 cell pellets were processed for TARGET retrieval and stained with the indicated rabbit antibodies, followed by HRP-anti rabbit and detected with ABC-peroxidase Elite. A) irrelevant rabbit antibody (R&D Systems) on Shh-293 cells; B) H-160 (Santa Cruz) on Shh-293 cells; on Shh-293 cells; 59A+B affinity purified polyclonal on Shh-293 (C) or untransfected (D) purified 95.9 rMab on Shh 293 (E) and untransfected (F) cells. Samples A, B and D were subjected to TSA-HRP amplification, resulting in some background staining, so this step was 5 omitted from the remaining samples. Scale bar is 50 µm.

Two rabbit polyclonal antibodies were raised to human Shh-N expressed in *E. coli* with an N-terminal unizyme tag. Both rabbits 59A and 59B responded well, with titers of 1:200 000 and over 1:2 million, respectively, by the 11$^{th}$ week of boosting. All bleeds with a titer of over 1:7000 were pooled and affinity purified on the antigen, and the resulting antibody compared with the current "gold standard" H-160 antibody (Santa Cruz Biotechnology) by immunofluorescence (IF), immunohistochemistry (IHC) and Western blotting of Shh-transfected cells. The rabbit polyclonal stained Shh in the endoplasmic reticulum of stably transfected Shh-COS cells (FIG. 1A), similar to the staining obtained with H-160 (FIG. 1C), but with some nuclear background evident in untransfected COS cells (FIG. 1B). It also recognized Shh in the cytoplasm (most likely endoplasmic reticulum) and cell membrane of formalin-5 fixed, paraffinembedded 293 cell pellets by IHC (FIG. 2C), again with some background staining in untransfected cells (FIG. 2D), but otherwise slightly stronger than to H-160 staining (FIG. 2B).

Rabbit monoclonal antibodies (rmAbs) not only provide a theoretically unlimited supply of reagent, but also have the advantage of recognizing a more specific epitope with higher affinity than a mixed polyclonal. The spleen of the higher titer rabbit 59B was therefore fused with rabbit myeloma cells to generate rabbit hybridomas. The 96-well supernatants of these were screened by ELISA on the Shh-N antigen (data not shown) and further expanded and selected for reactivity by IF and IHC as above. Of 32 initial ELISA+ parental clones, one (clone #95) remained positive following subcloning and the three strongest IHC+ subclones were selected: 95.3, 95.7 and 95.9. All three subclones are likely identical, based on their similar immunostaining of Shh-transfected cells (FIG. 3 top row) and virtually identical Nterminal sequences (FIG. 4A), although the presence of endogenous (non-Shh reactive) heavy chain from the myeloma fusion partner complicated the sequence analysis.

Due to its greater yield, 95.9 was selected for scale up and purification. It recognized Shh in transfected cells by IF (FIG. 1E) and IHC (FIG. 2E), but was cleaner than the polyclonal from which it was derived, as judged by the much reduced background staining on untransfected cells by IF (FIG. 1F, 2D). 95.9 rmAb did not require TSA amplification in order to detect its antigen. The staining of Shh-transfected cells was specific because another rabbit monoclonal antibody (R&D systems catalog number 269518) to an irrelevant antigen only resulted in background cytoplasmic staining (FIG. 2A and data not shown). Furthermore, the Shh-specific staining was stronger than that of the H-160 antibody (compare FIG. 2E with 2B).

Although raised against Shh-N, 95.9 and its sister clones 95.3 and 95.7 cross-react with the 89% identical Ihh-N and 74% identical Dhh-N, as judged by IF (FIG. 3A), IHC (data not shown), and Western blotting (FIG. 3B) of transfected full-length clones, similar to H-160, thus we henceforth refer to these antibodies as anti-Hh. By Western blotting, both the full length Hh (~50 kDa) unprocessed ER form of Hh and the cleaved Hh-N (~25 kDa) were detected in transfected cells (although in stable Shh/COS cells where there is less total Shh expression, the full length band is less obvious or absent (data not shown). The ~95 kDa band detected by H-160, which is thought to be non-specific, due to its size and presence in untransfected cells, was not recognized in untransfected cells by 95.9 (although it did appear in the Dhh-transfected cells, where it is presumably some kind of Dhh dimer). All three anti-Hh clones and H-160 also cross-reacted with mouse Shh-N using all three techniques (data not shown), as expected since there is only one amino acid difference (Ser 67 of the human sequence is Thr in mouse), allowing us to stain mouse embryos as one means of validating the specificity and sensitivity of 95.9.

The epitope of 95.9 was mapped by tryptic digestion of his-tagged hShh to residues 75-96, which are 100% identical in hIhh, and are only 3 aa different in hDhh (FIG. 5) thus suggesting that 95.9 will detect Shh and Ihh with similar, if not identical sensitivity, as well as explaining the ability of the antibody to cross-react with all three ligands. Additionally, this peptide is found on the opposite face of Shh to the previously established Ptc and 5E1 blocking antibody binding sites {Pepinsky, 2000 #4}, which supports the inability of 95.9 to compete with 5E1 for Hh binding (data not shown, but see FIG. 11.

Figure 6:
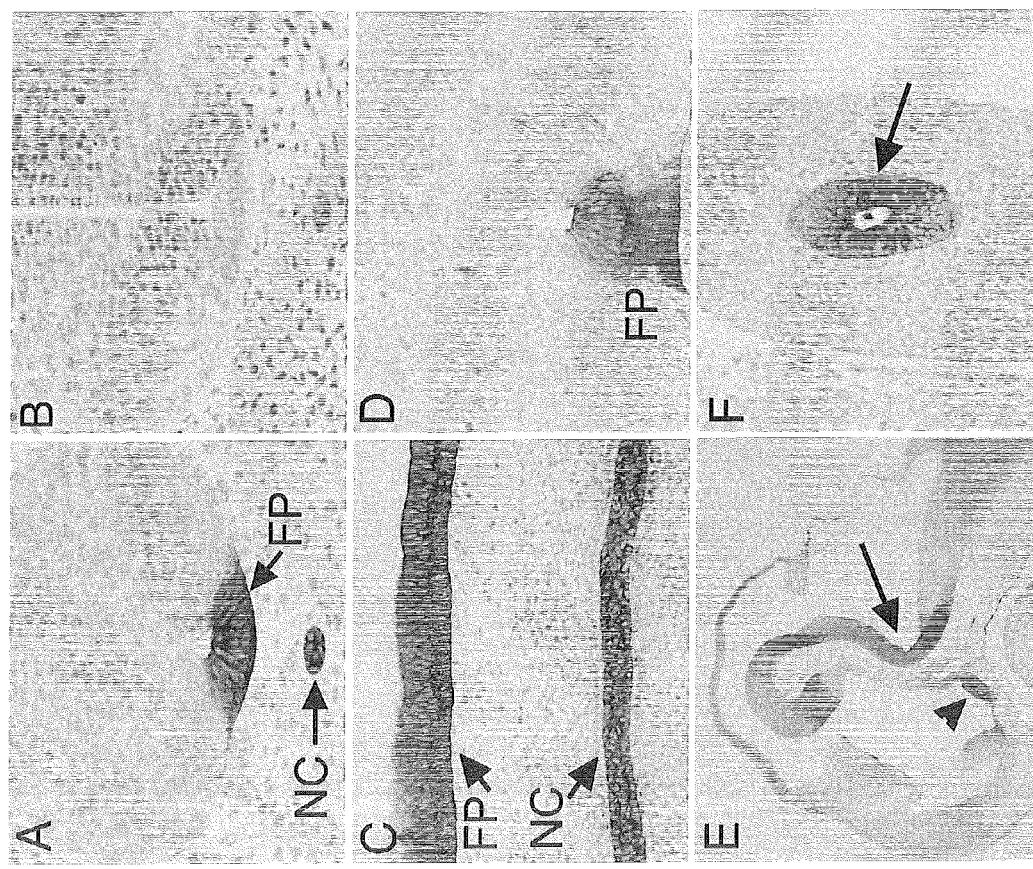
FIGS. 6A-F are micrographs showing, via IHC staining, that 95.9 recognizes endogenous Hh in the expected regions of developing mouse embryos. A) 95.9 stains Hh in the ventral neural tube floorplate (FP) and notochord (NC) of a transverse section of an E10.5 mouse embryo much more strongly than the H-160 antibody under the same conditions (both without TSA amplification) (B). C) E11.5 saggital section of neural tube floorplate (FP) and notochord (NC) stained by 95.9. D) E11.5 embryo showing a possible diffusion gradient of Hh from the ventral floor plate along the neural tube (arrows). E) 95.9 stains the neuroepithelium of the developing brain of an E11.5 mouse shown at lower magnification. TV, telecephalic vesicle; 4th ventricle. F) E11.5 transverse section through the developing mid-gut, showing the expected expression in epithelial cells surrounding the lumen (arrow) and absence of signal in the surrounding mesenchyme.

95.9 anti-Hh rmAb Shows Greater Sensitivity and Specificity than the H-160 Polyclonal by IHC Staining Several anti-Hh antibodies have been shown to recognize recombinant Hh, but staining of the lower levels present in endogenous tissues or tumors has been less successful, especially in FFPE specimens (refs). Since 95.9 was selected for its ability to recognize FFPE-fixed Hh, it was of interest to determine if it was sensitive and specific enough to detect endogenous Hh. To this end, we examined developing mouse embryos, since the distribution of Shh mRNA during development has been well documented by in situ hybridization (ISH) to be abundant at the E10.5 stage in the notochord and floorplate of the ventral neural tube from where Shh is thought to diffuse and create a morphogen gradient to specify the fate of the various neurons in the neural tube (refs); as well as in the mid-gut, where it is implicated in the morphogenesis of the gut epithelium {Bitgood, 1995 #1} and in hind limb buds, where it regulates proper digit formation {Chuong, 2000 #2; Johnson, 1994 #3}. Direct evidence that the mRNA is translated comes from notochord and floorplate staining of frozen embryos with the monoclonal anti-Shh antibody 5E1 (ref), but this antibody insufficiently stains shh in FFPE fixed specimens such as routine tumor biopsies, thus limiting its potential as a diagnostic for putative Hh-expressing tumors. In contrast, the anti-Shh antibody 95.9 specifically stained the notochord and ventral floor plate of E10.5 mouse embryos (brown stain in FIG. 6A), much more strongly than the H-160 antibody (FIG. 6B) under the same staining conditions (which were previously found also to be optimal for H-160 on Shh/293 cell pellets). At E11.5, not only the ventral neural tube and floorplate were obvious (FIG. 6C), but also faint staining of structures extending away from the floorplate (FIG. 6D). While this could be consistent with the postulated role of Hh as morphogen, this should be confirmed by ISH to confirm any overlap with Gli1 or Ptc1 to determine if this expression is real, as Shh mRNA would not overlap in the receiving cells)). If real, it would be suggestive of the first direct visualization of Hh gradient. Hh staining was also present in the neuroepithelium developing brain between the telecephalic vesicle and 4th ventricle (E11.5; FIG. 6E) as well as the mid-gut epithelium (FIG. 6F), as expected from earlier ISH results. There was no staining in any parts of the embryo where Hh was not expected to be found, illustrating the specificity of 95.9.

As a further test for 95.9 sensitivity, we analyzed by IHC a panel of 36 human colon cancer cell lines in which we had pre-determined mRNA levels for Shh (and Ihh and Dhh) by Q-PCR. The critical threshold (Ct) values for Shh ranged from undetectable in RKO and Colo320 cells (below a Ct of 38) to 24 for the highest expressing cell lines. Importantly, none of the cell lines that lacked all three Hh mRNAs (such as DLD-1) showed any staining with 95.9, thereby demonstrating specificity of the antibody to hedgehog. Based on cytoplasmic and membranous staining of Hh by 95.9, various cell lines could be grouped into three positive categories: low (scored as 1+; e.g. FIG. 7B); moderate (2+; e.g. FIG. 7C) or high (3+; e.g. FIG. 7D) Hh-expressing. The ΔCt values following normalization to the housekeeping gene β-glucuronidase (GUSB) were plotted versus IHC scores, illustrating a trend towards higher IHC scores with higher mRNA values (lower ΔCt values), with a Spearman coefficient of −5 0.61 (FIG. 7E). The correlation was not perfect because some of the cell lines also express Ihh, which is likely equally well recognized by 95.9 (based on 100% sequence identity in the epitope; FIG. 5), in addition to Shh (notably the 3+ cell line SW403 and the 2+ cell line HT29), but nonetheless is statistically significant (p=0.0001). These data suggest that 95.9 can usefully identify Hh-expressing FFPE-processed cancer cell lines by IHC. Importantly, two of the colorectal xenograft cell lines that respond well to GDC-0449 (and 5E1) in vivo, LS180 and HT55 (data not shown), express Hh at only 1+ levels (FIG. 7E), suggesting that it may be the presence of Hh per se, rather than high expression of Hh that is important in tumor selection for Hh antagonist therapy. In this respect, the higher sensitivity of 95.9 than H160 may allow it to detect a higher proportion of 1+ expressors and therefore makes it a better diagnostic antibody.

Figure 8:
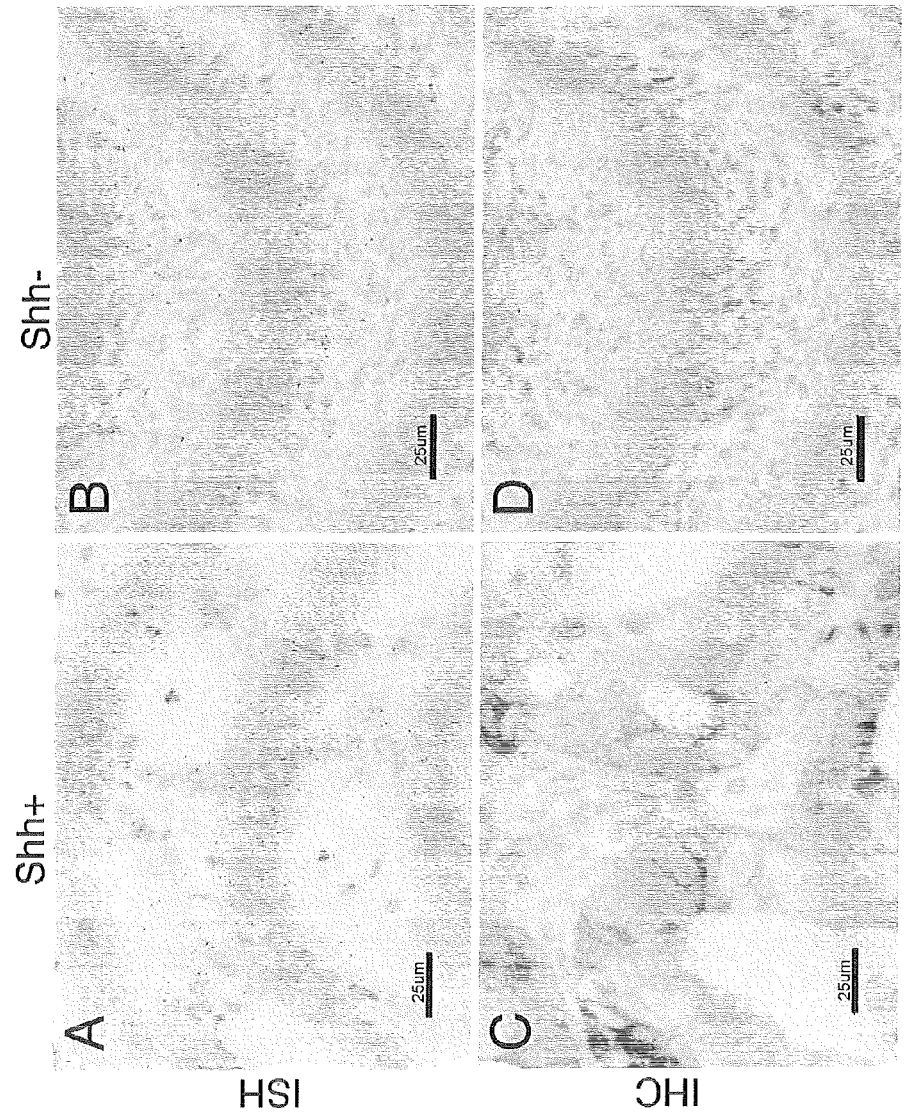
FIGS. 8A-D show that 95.9 stains Shh+, but not Shh−, ovarian cancer specimens. In situ hybridization of human ovarian cancer specimens with an antisense probe to Shh shows one specimen expresses Shh mRNA (black dots) in the tumor epithelium A) and the other B) does not show any more signal than the sense probe background (not shown). 95.9 staining of the same tumors shows positive cytoplasmic and membranous signal (brown) in only the Shh+ tumor epithelium C), and not the Shh-negative specimen D). Scale bar is 25 Om.

Detection of Hh in primary human tumor biopsies could be useful for selection of type III (paracrine Hh-ligand-driven) cancer patients for therapy with Hh antagonists, since tumors that do not express Hh would be unlikely to respond such therapy. We therefore sought to determine if 95.9 was capable of detecting Hh in a human ovarian tumor that had previously been shown to express Shh by ISH. Indeed, 95.9 gave robust labeling of the Shh-(+) but not a different Shh-(−) ovarian tumor (FIG. 8), confirming its utility and specificity.

Encouraged by the specificity and apparently superior sensitivity of 95.9 to H-160, we proceeded to determine the prevalence of Hh expression in a larger array of specimens from ovary (72 tumors and 2 normal, data not shown), colon (99 tumors and 44 normal) and pancreas (105 tumors and 17 normal) and classified the cytoplasmic staining as absent (0+), weak (1+), moderate (2+) or strong (3+), with representative images from each category for each tissue type being shown in FIG. 9A. Approximately 20% of both tumor and normal colon samples (FIG. 9B) lacked specific cytoplasmic and membranous Hh staining (any nuclear background was considered non-specific, since Hh is not expected to be present in this part of the cell). The remaining 80% were Hh-positive, with mostly 1+ expression (68% tumors and 54% normal), fewer with 2+ expression (10% tumor and 23% normal) and even fewer with strong 3+ staining (3% tumor and no normal). Similarly, low expression was found in most of the ovarian samples (57% tumor and 2/2 normal were considered 1+), with 31% in the 2+ and 6% in the 3+ categories and 7% negative tumors. Likewise, 23% of 105 pancreatic tumors were considered negative, compared to 41% of normal pancreas specimens; 70% of tumors and 41% normal expressed low (1+) levels of Hh; 7% of tumors and 18% of normals expressed 2+ levels, and no specimens displayed strong staining. These results indicate that while Hh expression does not appear to be much stronger in tumors than normal tissues, there is a range of expression among specimens. Importantly, up to 23% tumor samples lacked Hh expression in this analysis, suggesting that it may be worthwhile to evaluate Hh expression in patients undergoing clinical trials with Hh antagonists to determine if any lack of response correlates with lack of Hh expression. It is also possible that that anti-Hh antibodies of the invention can be used to determined if Hh expression level correlates with response to antagonist treatment.

Figure 10:
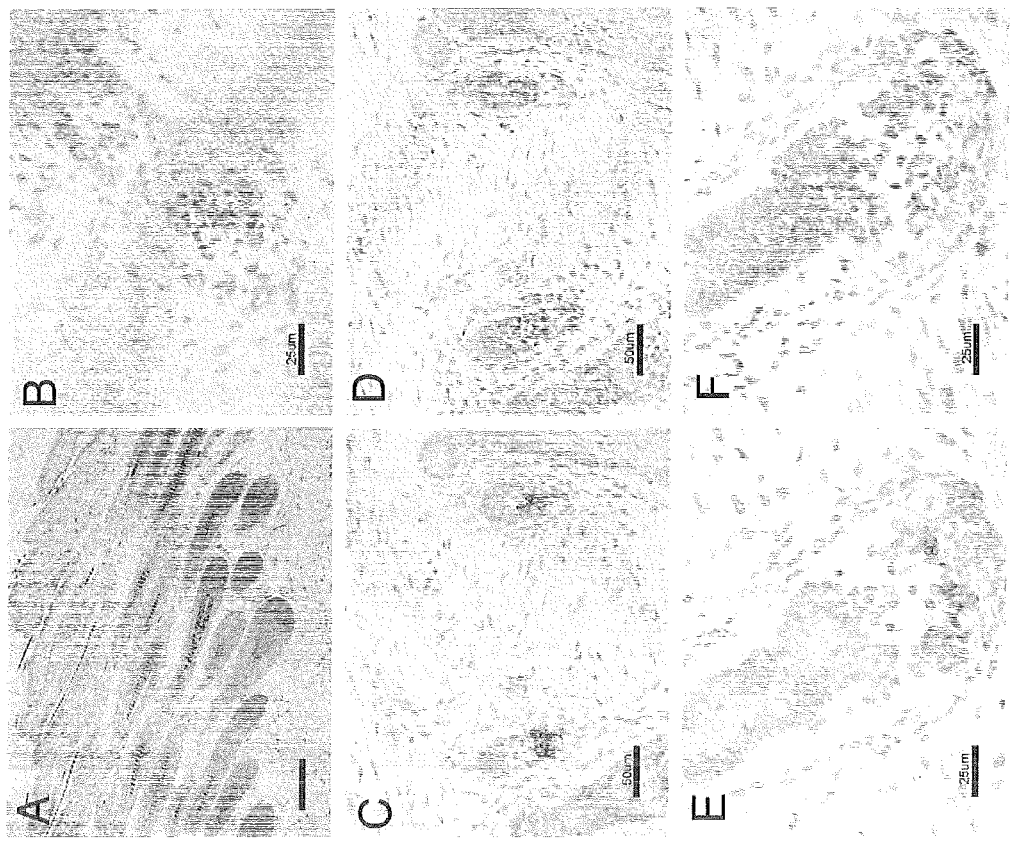
FIGS. 10A-F show by IHC staining that anti-Hh Ab 95.9 is sufficiently sensitive to detect low levels of Hh in hair follicles. A) C57BL/6 4-week old mice skin labeled by 95.9 reveals Shh signal in the hair follicles at 4 weeks of age when the hair is in anagen phase. B) In situ hybridization of a longitudinal section of fetal human skin (scalp) using an antisense Shh probe, showing signal in the outer root sheath. Transverse section of fetal human scalp stained with 95.9 (C) or H160 (D). Longitudinal sections of fetal human scalp stained with 95.9 (E) or H160 (F), showing staining in the proximal epithelium above the dermal papilla, consistent with the ISH signal in (B). Scale-bar is 50 µm in C, D and 25 µm in all other panels.

Finally, we wanted to determine the sensitivity of the anti-Hh antibody 95.9 in a low expressing tissue, such as hair follicles. Hh mRNA has been detected by in situ hybridization in hair follicles {Iseki, 1996 #8} and furthermore, injection of the blocking antibody 5E1 or the Hh antagonist cyclopamine prevents hair development in mouse embryos {Wang, 2000 #6}; {Chiang, 1999 #10}, thus strongly suggesting that Hh signaling in this organ is essential. However, Hh protein has not been demonstrated in the hairs of FFPE skin specimens by IHC, most likely due inadequate antibody sensitivity. Hh signaling is known to be elevated during the anagen phase of hair growth, with less activity during telogen {Sato, 1999 #9} and in adult mice, hair growth is synchronized such that anagen occurs at 4 weeks of age and showed a robust signal at this stage of growth for both Shh protein (FIG. 10A), as detected by 95.9 staining. In humans, hair growth is not synchronized, but a subset of follicles should be in anagen phase at any given time. Indeed, we observed approximately 10% hair follicles from human fetal scalp showing Shh-specific signal using an antisense (FIG. 10B) but not a sense probe (Data not shown). Accordingly, a subset of hair follicles showed 95.9-reactivity, with well-defined staining in the proximal epithelium above the dermal papilla (FIG. 10 C,E), much stronger than the very faint staining obtained with H160 (FIG. 10D, F). Thus, 95.9 is sensitive enough to detect low levels of Hh in anagen hair follicles and is superior to the H160 antibody in this respect. This suggests that 95.9 is likely to detect a greater proportion of Hh-expressing tumor samples than H160 and so is the reagent of choice for development of an IHC kit for clinical selection of prospective patients for Hh-antagonist therapy.

Example 2

Microarray Analysis to Detect Downregulation of Hedgehog Polypeptides in Cancer or Tumors Nucleic acid microarrays, often containing thousands of gene sequences, are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition.

The methodology of hybridization of nucleic acids and microarray technology is well known in the art. In the present example, the specific preparation of nucleic acids for hybridization and probes, slides, and hybridization conditions are all detailed in PCT Patent Application Serial No. PCT/US01/10482, filed on Mar. 30, 2001 and which is herein incorporated by reference.

Example 3

Quantitative Analysis of Hedgehog mRNA Expression

In this assay, a 5' nuclease assay (for example, TaqMan) and real-time quantitative PCR (for example, ABI Prism 7700® Sequence Detection System (Perkin Elmer, Applied Biosystems Division, Foster City, Calif.)), is used to find genes that are significantly overexpressed in a cancerous glioma tumor or tumors as compared to other cancerous tumors or normal non-cancerous tissue. The 5' nuclease assay reaction is a fluorescent PCR-based technique which makes use of the 5' exonuclease activity of Taq DNA polymerase enzyme to monitor gene expression in real time. Two oligonucleotide primers (whose sequences are based upon the gene or EST sequence of interest) are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the PCR amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative and quantitative interpretation of the data. This assay is well known and routinely used in the art to quantitatively identify gene expression differences between two different human tissue samples, see, e.g., Higuchi et al., Biotechnology 10:413-417 (1992); Livak et al., PCR Methods Appl., 4:357-362 (1995); Heid et al., Genome Res. 6:986-994 (1996); Pennica et al., Proc. Natl. Acad. Sci. USA 95(25):14717-14722 (1998); Pitti et al., Nature 396(6712):699-703 (1998) and Bieche et al., Int. J. Cancer 78:661-666 (1998).

The 5' nuclease procedure is run on a real-time quantitative PCR device such as the ABI Prism® 7700 Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

The starting material for the screen is mRNA isolated from a variety of different cancerous tissues. The mRNA is quantitated precisely, e.g., fluorometrically. As a negative control, RNA is isolated from various normal tissues of the same tissue type as the cancerous tissues being tested. Frequently, tumor sample(s) are directly compared to "matched" normal sample(s) of the same tissue type, meaning that the tumor and normal sample(s) are obtained from the same individual.

5' nuclease assay data are initially expressed as Ct, or the threshold cycle. This is defined as the cycle at which the reporter signal accumulates above the background level of fluorescence. The ΔCt values are used as quantitative measurement of the relative number of starting copies of a 5 particular target sequence in a nucleic acid sample when comparing cancer mRNA results to normal human mRNA results. As one Ct unit corresponds to 1 PCR cycle or approximately a 2-fold relative increase relative to normal, two units corresponds to a 4-fold relative increase, 3 units corresponds to an 8-fold relative increase and so on, one can quantitatively and quantitatively measure the relative fold increase in mRNA expression between two or more different tissues. In this regard, it is well accepted in the art that this assay is sufficiently technically sensitive to reproducibly detect an at least 2-fold increase in mRNA expression in a human tumor sample relative to a normal control.

Example 4

In situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization is performed following an optimized version of the protocol by Lu and Gillett, *Cell Vision* 1:169-176 (1994), using PCR-generated $^{33}$P-labeled riboprobes. Briefly, formalin-fixed, paraffin-embedded human tissues are sectioned, deparaffinized, deproteinated in proteinase K (20 g/ml) for 15 minutes at 37° C., and further processed for in situ hybridization as described by Lu and Gillett, supra. A [$^{33}$-P] UTP-labeled antisense riboprobe are generated from a PCR product and hybridized at 55° C. overnight. The slides are dipped in Kodak NTB2 nuclear track emulsion and exposed for 4 weeks.

$^{33}$P-Riboprobe Synthesis 6.0 μl (125 mCi) of $^{33}$P-UTP (Amersham BF 1002, SA<2000 Ci/mmol) were speed vac dried. To each tube containing dried $^{33}$P-UTP, the following ingredients were added:
2.0 μl 5× transcription buffer
1.0 μl DTT (100 mM)

2.0 nl NTP mix (2.5 mM:10μ; each of 10 mM GTP, CTP & ATP+10 μl H2O)
1.0 μl UTP (50 μM)
1.0 μl Rnasin
1.0 μl DNA template (1 μg)
1.0 μl H$_2$O
1.0 μl RNA polymerase (for PCR products T3=AS, T7=S, usually)

The tubes are incubated at 37° C. for one hour. 1.0 μl RQ1 DNase is added, followed by incubation at 37° C. for 15 minutes. 90 μl TE (10 mM Tris pH 7.6/1 mM EDTA pH 8.0) are added, and the mixture was pipetted onto DE81 paper. The remaining solution is loaded in a Microcon-50 ultrafiltration unit, and spun using program 10 (6 minutes). The filtration unit is inverted over a second tube and spun using program 2 (3 minutes). After the final recovery spin, 100 μl TE is added. 1 μl of the final product is pipetted on DE81 paper and counted in 6 ml of Biofluor II.

The probe is run on a TBE/urea gel. 1-3 μl of the probe or 5 μl of RNA Mrk III is added to 3 μl of loading buffer. After heating on a 95° C. heat block for three minutes, the probe is immediately placed on ice. The wells of gel are flushed, the sample loaded, and run at 180-250 volts for 45 minutes. The gel is wrapped in saran wrap and exposed to XAR film with an intensifying screen in −70° C. freezer one hour to overnight.

$^{33}$P-Hybridization

A. Pretreatment of Frozen Sections

The slides are removed from the freezer, placed on aluminum trays and thawed at room temperature for 5 minutes. The trays are placed in 55° C. incubator for five minutes to reduce condensation. The slides are fixed for 10 minutes in 4% paraformaldehyde on ice in the fume hood, and washed in 0.5×SSC for 5 minutes, at room temperature (25 ml 20×SSC+975 ml SQ H$_2$O). After deproteination in 0.5 μg/ml proteinase K for 10 minutes at 37° C. (12.5 μl of 10 mg/ml stock in 250 ml prewarmed RNase-free RNAse buffer), the sections are washed in 0.5×SSC for 10 minutes at room temperature. The sections are dehydrated in 70%, 95%, 100% ethanol, 2 minutes each.

B. Pretreatment of Paraffin-Embedded Sections

The slides are deparaffinized, placed in SQ H2O, and rinsed twice in 2×SSC at room temperature, for 5 minutes each time. The sections are deproteinated in 20 μg/ml proteinase K (500 μl of 10 mg/ml in 250 ml RNase-free RNase buffer; 37° C., 15 minutes)—human embryo, or 8× proteinase K (100 μl in 250 ml Rnase buffer, 37° C., 30 minutes)—formalin tissues. Subsequent rinsing in 0.5×SSC and dehydration are performed as described above.

C. Prehybridization

The slides are laid out in a plastic box lined with Box buffer (4×SSC, 50% formamide)-saturated filter paper.

D. Hybridization 1.0×10$^6$ cpm probe and 1.0 μl tRNA (50 mg/ml stock) per slide are heated at 95° C. for 3 minutes. The slides are cooled on ice, and 48 μl hybridization buffer are added per slide. After vortexing, 50 μl $^{33}$P mix are added to 50 μl prehybridization on slide. The slides are incubated overnight at 55° C.

E. Washes

Washing is done 2×10 minutes with 2×SSC, EDTA at room temperature (400 ml 20×SSC+16 ml 0.25M EDTA, V=4L), followed by RNaseA treatment at 37° C. for 30 minutes (500 μl of 10 mg/ml in 250 ml Rnase buffer=20 μg/ml). The slides are washed 2×10 minutes with 2×SSC, EDTA at room temperature. The stringency wash conditions can be as follows: 2 hours at 55° C., 0.1×SSC, EDTA (20 ml 20×SSC+16 ml EDTA, V$_f$=4L).

F. Oligonucleotides

In situ analysis is performed on a variety of DNA sequences disclosed herein. The oligonucleotides employed for these analyses is obtained so as to be complementary to the nucleic acids (or the complements thereof) as shown in the accompanying figures.

Example 5

Expression of anti-Hh Antibody in *E. coli*

This example illustrates preparation of an unglycosylated form of anti-hedgehog antibody by recombinant expression in *E. coli*.

The DNA sequence encoding the preceding antibody sequences is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., Gene, 2:95 (1977)) which contains genes for ampicillin and tetracycline resistance. The vector is digested with restriction enzyme and dephosphorylated. The PCR amplified sequences are then ligated into the vector.

The vector will preferably include sequences which encode for an antibiotic resistance gene, a trp promoter, a polyhis leader (including the first six STII codons, polyhis sequence, and enterokinase cleavage site), the anti-hedghog antibody coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized heavy and light chains of the anti-hedgehog antibody can then be purified using a metal chelating column under conditions that allow tight binding of the protein.

The preceding heavy and light chain polypeptide sequences may be expressed in *E. coli* in a poly-His tagged form, using the following procedure. The DNA encoding heavy and light chains of the antihedgehog antibody is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g (NH$_4$)$_2$SO$_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM MgSO$_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 10 M guanidine, 20 mM Tris, pH 8 buffer. Solid sodium sulfite and sodium tetrathionate is added to make final concentrations of 0.1 M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros® R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded protein are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 6

Expression of Anti-Hedgehog Antibody 5 in Mammalian Cells

This example illustrates preparation of a potentially glycosylated form of anti-hedgehog antibody by recombinant expression in mammalian cells.

The vector, pRK5 (see EP 307,247, published Mar. 15, 1989), may be employed as the expression vector. Optionally, DNA encoding the heavy and light chains of the anti-hedgehog antibody described herein is ligated into pRK5 with selected restriction enzymes to allow insertion of such DNA using ligation methods such as described in Sambrook et al., supra. The resulting vector is called anti-Hh-DNA.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-anti-Hh DNA is mixed with about 1 μg DNA encoding the VA RNA gene [Thimmappaya et al., Cell, 31:543 (1982)] and dissolved in 500 μl of 1 mM Tris-HCl, 0.1 mM EDTA, 0.227 M CaCl$_2$. To this mixture is added, dropwise, 500 μl of 50 mM HEPES (pH 7.35), 280 mM NaCl, 1.5 mM NaPO$_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of the heavy and light chains of the anti-hedgehog antibody. The cultures containing transfected cells may undergo further incubation (in serum free medium) and the medium is tested in selected bioassays.

In another embodiment, the anti-hedgehog antibody can be expressed in CHO cells. The pRK5-anti-Hh can be transfected into CHO cells using known reagents such as CaPO$^4$ or DEAE-dextran. As described above, the cell cultures can be incubated, and the medium replaced with culture medium (alone) or medium containing a radiolabel such as $^{35}$S-methionine. After determining the presence of the anti-Hh antibody, the culture medium may be replaced with serum free medium. Preferably, the cultures are incubated for about 6 days, and then the conditioned medium is harvested. The medium containing the expressed anti-Hh antibody can then be concentrated and purified by any selected method.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., Current Protocols of Molecular Biology, Unit 3.16, John Wiley and Sons (1997). CHO expression vectors are constructed to have compatible restriction sites 5= and 3=of the DNA of interest to allow the convenient shuttling of cDNA=s. The vector used expression in CHO cells is as described in Lucas et al., Nucl. Acids Res. 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents SUPERFECT® (Quiagen), DOSPER® or FUGENE® (Boehringer Mannheim). The cells are grown as described in Lucas et al., supra. Approximately $3 \times 10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3L production spinner is seeded at $1.2 \times 10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 Fm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 7

Purification of Anti-Hh Antibodies Using Anti-Hh Specific Antibodies

Native or recombinant anti-Hh antibodies may be purified by a variety of standard techniques in the art of protein purification. For example, pro-, mature or pre-polypeptide variants of the preceding heavy and light chain sequences are purified by immunoaffinity chromatography using antibodies specific for such sequences. In general, an immunoaffinity column is constructed by covalently coupling the respective heavy and light chains of the anti-Hh antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose® (Pharmacia LKB Biotechnology). The antibody is coupled to the resin, the resin is blocked, and the derivative resin is washed according to the manufacturer's instructions.

Such an immunoaffinity column is utilized in the purification of the preceding heavy and light chain sequences by preparing a fraction from cells containing such sequences in a soluble form. This preparation is derived by solubilization of the whole cell or of a subcellular fraction obtained via differential centrifugation by the addition of detergent or by other methods well known in the art. Alternatively, soluble heavy and light chain polypeptide containing a signal sequence may be secreted in useful quantity into the medium in which the cells are grown.

A soluble heavy and light chain preparations are passed over the immunoaffinity column, and the column is washed under conditions that allow the preferential absorbance of such sequences (e.g., high ionic strength buffers in the presence of detergent). Then, the column is eluted under conditions that disrupt the binding between the antibody/substrate (e.g., a low pH buffer such as approximately pH 2-3, or a high concentration of a chaotrope such as urea or thiocyanate ion), and the heavy and/or light chain polypeptide, respectively, is collected.

Example 7

Immunohistochemistry using Anti-Hh Antibodies

Experimental Design:

We examined Hh ligand protein expression in colorectal and ovarian carcinomas using 1 ug/ml and 5 ug/ml of 95.9 antibody. Twenty colorectal and 20 ovarian carcinomas were stained with 1 ug/ml and 5 ug/ml of the 95.9 anti-Hh antibody using a previously established protocol. Both a numeric and an alphanumeric scoring system were employed to capture the amount of tumor epithelial staining. The numeric scoring system estimates the total level of staining for each specimen (0=no staining, 1=weak, 2=moderate, 3=strong). The alphanumeric score captures 1) the % of tumor epithelium demonstrating any level of staining (0=no staining, 1=<25%, 2=25-75%, 3=>75%) and 2) the predominant intensity of staining (A=weak, B=moderate, C=strong). Tumors demonstrating less than 5% of tumor epithelium staining received a score of 0. The results are shown in Table 2. We found that a greater range of staining intensity was observed with 5 ug/ml primary antibody. We also found staining of Shh in neural tube cells with 95.5 and ovarian cancer cells, but not in normal ovarian tissue. Thus mAb 95.5 is a useful and sensitive antibody for diagnostic use in cancer, particularly in immunohistochemical staining

TABLE 2

| | Histologic Findings | |
|---|---|---|
| Sample No. | IHC (1 ug/ml) | IHC (5 ug/ml) |
| Colon Tumors | | |
| 1 | 1(1A) | 1(3A) |
| 2 | 1(3A) | 2(3A) |
| 3 | 0 | 1(2A) |
| 4 | 1(2A) | 2(3B) |
| 5 | 0 | 0 |
| 6 | 1(2A) | 2(3B) |
| 7 | 0 | 1(3A) |
| 8 | 0 | 1(2A) |
| 9 | 0 | 1(2A) |
| 10 | 0 | 1(3A) |
| | (focally strong) | (focally strong) |
| 11 | 0 | 1(3A) |
| 12 | 0 | 0 |
| 13 | 0 | 2(3A) |
| 14 | 0 | 1(2A) |
| 15 | 1(1B) | 2(2B) |
| 16 | 0 | 0 |
| 17 | 0 | 1(2A) |
| 18 | 0 | 1(2A) |
| 19 | 1(3A) | 2(3B) |
| 20 | 0 | 1(2A) |
| Ovary Tumors | | |
| 21 | 0 | 1(1B) |
| 22 | 1(2A) | 2(2B) punctate |
| 23 | 0 | 1(2A) |
| 24 | 1(1A) | 1(1B) |
| 25 | 0 | 1(3A) |
| 26 | 0 | 1(2A) punctate |
| 27 | 2(2B) | 2(2C) |
| 28 | 1(2A) | 2(2B) punctate |
| 29 | 0 | 1(3A) |
| 30 | 0 | 1(2A) |
| 31 | 0 | 1(2A) |
| 32 | 0 | 1(2A) |
| 33 | 0 | 1(2A) |
| 34 | 0 | 1(1A) |
| 35 | 0 | 1(3A) Punctate stromal |
| 36 | 0 | 0 |
| 37 | 0 | 1(2A) |
| 38 | 0 | 1(2A) |
| 39 | 0 | 1(1A) |
| 40 | 0 | 1(3A) |

The invention claimed is:

1. A method for detecting human sonic hedgehog expression in tissue and/or determining if the polypeptide is overexpressed in said tissue comprising the steps of:
 (a) removing a tissue sample from a tumor in a patient afflicted with the tumor;
 (b) contacting the tissue with an anti-human sonic hedgehog antibody comprising a heavy chain and a light chain, wherein the heavy chain comprises an HCHVR1 comprising the amino acid sequence of SEQ ID NO:2, an HCHVR2 comprising the amino acid sequence of SEQ ID NO:4 and an HCHVR3 comprising the amino acid sequence of SEQ ID NO:6 and the light chain comprising an LCHVR1 comprising the amino acid sequence of SEQ ID NO: 10, an LCHVR2 comprising the amino acid sequence of SEQ ID NO: 12 and an LCHVR3 comprising the amino acid sequence of SEQ ID NO: 14, wherein said anti-hedgehog antibody binds to the polypeptide at an epitope within the region of amino acid residues 75-96,
 (c) measuring the extent of binding; and
 (d) determining if human sonic hedgehog is overexpressed in said tissue, compared to normal tissue.

2. The method of claim 1, wherein the tissue sample is formalin-fixed paraffin-embedded (FFPE) prior to contacting with the anti-human sonic hedgehog antibody.

3. The method of claim 2, wherein the detection method is selected from the group consisting of immunohistochemistry (IHC) and Western blot.

* * * * *